US011220569B2

United States Patent
Parks et al.

(10) Patent No.: US 11,220,569 B2
(45) Date of Patent: Jan. 11, 2022

(54) POROUS MATERIAL AND METHODS RELATED THERETO

(71) Applicant: Southern Research Institute, Birmingham, AL (US)

(72) Inventors: William Madison Parks, Birmingham, AL (US); Rebecca J. Boohaker, Birmingham, AL (US); Ashish Pathak, Birmingham, AL (US); Saibal Chakraborty, Birmingham, AL (US)

(73) Assignee: SOUTHERN RESEARCH INSTITUTE, Birmingham, AL (US)

( * ) Notice: Subject to any disclaimer, the term of this patent is extended or adjusted under 35 U.S.C. 154(b) by 179 days.

(21) Appl. No.: 16/247,018

(22) Filed: Jan. 14, 2019

(65) Prior Publication Data

US 2019/0276580 A1 Sep. 12, 2019

Related U.S. Application Data

(62) Division of application No. 15/096,882, filed on Apr. 12, 2016, now Pat. No. 10,450,399.

(51) Int. Cl.
| | | |
|---|---|---|
| *C08J 9/28* | (2006.01) | |
| *C08G 8/22* | (2006.01) | |
| *C12Q 1/6816* | (2018.01) | |
| *B01J 13/00* | (2006.01) | |

(52) U.S. Cl.
CPC ............ *C08G 8/22* (2013.01); *B01J 13/0091* (2013.01); *C12Q 1/6816* (2013.01)

(58) Field of Classification Search
CPC ....... C08G 8/22; B01J 13/0091; C12Q 1/6816
See application file for complete search history.

(56) References Cited

U.S. PATENT DOCUMENTS

| | | | |
|---|---|---|---|
| 4,873,218 A | 10/1989 | Pekala | |
| 4,903,766 A | 2/1990 | Shu | |
| 4,997,804 A | 3/1991 | Pekala | |
| 5,081,163 A | 1/1992 | Pekala | |
| 5,260,855 A | 11/1993 | Kaschmitter et al. | |
| 5,402,306 A | 3/1995 | Mayer et al. | |
| 5,420,168 A | 5/1995 | Mayer et al. | |
| 5,508,341 A | 4/1996 | Mayer et al. | |
| 5,529,971 A | 6/1996 | Kaschmitter et al. | |
| 5,945,084 A * | 8/1999 | Droege ................. | H01G 11/26 423/447.4 |
| 6,288,132 B1 | 9/2001 | Schwarz | |

(Continued)

FOREIGN PATENT DOCUMENTS

| | | |
|---|---|---|
| CN | 102302917 A | 1/2012 |
| CN | 103933900 A | 7/2014 |

OTHER PUBLICATIONS

Al-Muhtaseb, et al., "Preparation and Properties of Resorcinol-Formaldehyde Organic and Carbon Gels", Adv. Mater, 2003, 15, No. 2, Jan. 2003 (14 pages).

(Continued)

*Primary Examiner* — Kara B Boyle
(74) *Attorney, Agent, or Firm* — Ballard Spahr LLP

(57) ABSTRACT

Disclosed herein is an aerogel made from a polyhydroxy benzene compound crosslinked with formaldehyde. The aerogel is dry and has a first volume and wherein the aerogel can be exposed to a liquid and be re-dried in a gas while retaining at least 70% of the first volume.

20 Claims, 17 Drawing Sheets

(56) References Cited

U.S. PATENT DOCUMENTS

| | | | |
|---|---|---|---|
| 2004/0152085 A1* | 8/2004 | Terlesky | B01J 20/3219 |
| | | | 435/6.12 |
| 2006/0286360 A1* | 12/2006 | Rhine | C09C 3/12 |
| | | | 428/221 |
| 2009/0000983 A1 | 4/2009 | Brown et al. | |
| 2013/0066063 A1 | 3/2013 | Berry et al. | |

OTHER PUBLICATIONS

Gunko, et al., "Synthesis and characterization of resorcinol—formaldehyde resinchars doped by zinc oxide", (2014) Applied Surface Science (9 pages).

Horikawa, et al., "Size control and characterization of spherical carbon aerogel particles from resorcinol-formaldehyde resin", Carbon 42 (2004) (8 pages).

Liang, et al., "Resorcinol-formaldehyde aerogels prepared by supercritical acetone drying", Journal of Non-Crystalline Solids, vol. 271 (2000) pp. 167-170.

Mulik, et al., "Resorcinol-Formaldehyde Aerogels—Chapter 11" Aerogels Handbook, Advances in Sol-Gel Derived Materials and Technologies (2011) (20 pages).

Mulik, et al., "Time-Efficient Acid-Catalyzed Synthesis of Resorcinol-Formaldehyde Aerogels", Chem. Mater. 2007, vol. 19, pp. 6138-6144.

Pekala, (1989) "Organic aerogels from the polycondensation of resorcinol with formaldehyde" J. Mat. Sci., vol. 24, pp. 3221-3227.

Tamon, et al., (1998) "SAXS Study on Gelation Process in Preparation of Resorcinol—Formaldehyde Aerogel", J. Colloid and Interface Sci., vol. 206, pp. 577-582.

Definition of Catalyst. Dictionary.com. 2018. (Year: 2018).

* cited by examiner

POROUS MATERIAL AND METHODS RELATED THERETO

BACKGROUND

Historical routes to resorcinol-formaldehyde aerogels yield hydrogels which must be supercritically dried in order to retain their nano-porous properties. Even after supercritical drying, exposure to liquids will cause catastrophic failure of the material. Several routes to air-dried aerogels have been published to yield material that can be processed and dried at atmospheric pressure, but have the same catastrophic failure as the supercritically dried aerogel when exposed to liquids.

Phenol formaldehyde polymers have been studied for over 100 years. Acid catalyzed polymers with excess phenol are called Novolacs and base catalyzed polymers with excess formaldehyde are called Resoles. Resorcinol-formaldehyde aerogels were invented in the 1990s. The most common catalyst is sodium carbonate (a base).

Paul Shu (U.S. Pat. No. 4,903,766 (1990)) uses aluminum acetate as a crosslinker for resorcinol and formaldehyde to form a gel that is used to seal pores in oil wells. This application is an in-situ gel formation that forms selectively in the porous structure around the oil well, but it does not form an aerogel.

Accordingly, there is a need for aerogels that do not experience catastrophic failure when exposed to liquids. Disclosed herein are such aerogels and methods related thereto.

BRIEF SUMMARY

Disclosed herein is an aerogel comprising a polyhydroxy benzene compound crosslinked with formaldehyde, wherein the aerogel is dry and has a first volume, wherein the aerogel can be exposed to a liquid and be re-dried in a gas while retaining at least 70% of the first volume.

Also disclosed herein is a device comprising the aerogel disclosed herein.

Also disclosed herein is a method of making an aerogel comprising the steps of: a) crosslinking a polyhydroxy benzene compound with formaldehyde in the presence of an aluminum catalyst, thereby forming a gel having a first volume; and b) drying the gel in gas, thereby forming an aerogel having a second volume.

Also disclosed herein is a method of detecting a biological condition in a subject comprising the steps of: a) incubating a sample with an aerogel disclosed herein; and b) detecting the presence or absence of a biomarker for a biological condition in the sample using the signaling moiety of the aerogel.

Also disclosed herein is a method comprising a) incubating a sample obtained from a subject with an aerogel disclosed herein; and b) determining the presence or absence of a biomarker for a biological condition in the sample using the signaling moiety of the aerogel, wherein the presence of the biomarker indicates the subject has a biological condition, wherein the absence of the biomarker indicates the subject does not have a biological condition.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 13A shows the assay as limited by background from a white nitrocellulose membrane in a traditional AuNP lateral flow assay. In FIG. 13B, the dotted line represents the interference of background scattering, severely limiting the sensitivity of the assay.

DETAILED DESCRIPTION

Figure 1:
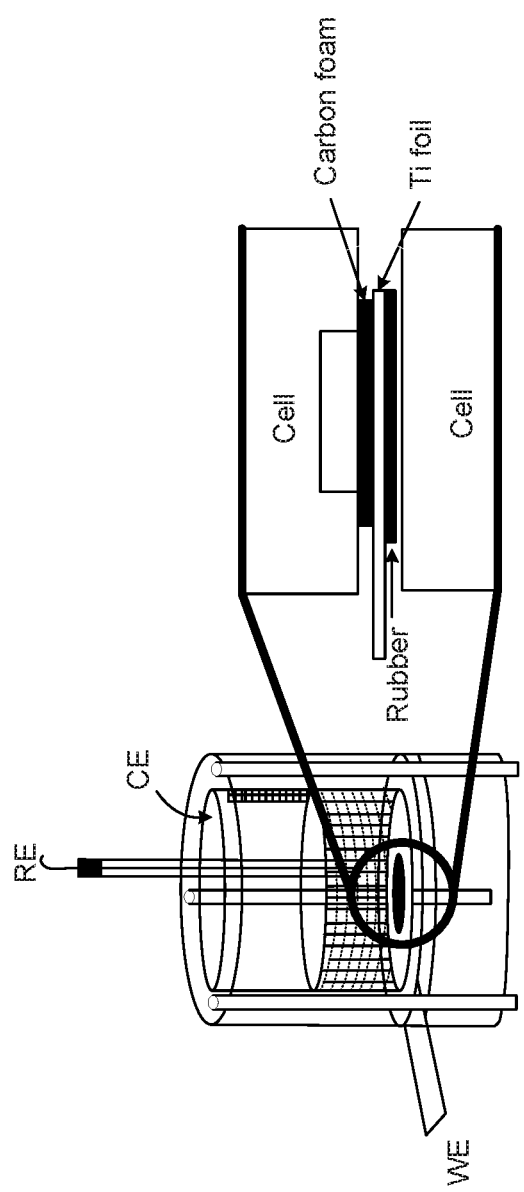
FIG. 1 shows a schematic of a 3-electrode system.

The disclosed method and compositions may be understood more readily by reference to the following detailed description of particular embodiments and the Example included therein and to the Figures and their previous and following description It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Materials

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if an aerogel is disclosed and discussed and a number of modifications that can be made to a number of materials including the aerogel, then each and every combination and permutation of the aerogel and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Definitions

As used herein, the term "subject" or "patient" refers to any organism to which a composition of this invention may be administered, e.g., for experimental, diagnostic, and/or therapeutic purposes. Typical subjects include animals (e.g., mammals such as non-human primates, and humans; avians; domestic household or farm animals such as cats, dogs, sheep, goats, cattle, horses and pigs; laboratory animals such as mice, rats and guinea pigs; rabbits; fish; reptiles; zoo and wild animals) and/or plants. Typically, "subjects" are animals, including mammals such as humans and primates; and the like.

The term "biomarker" refers to a measurable substance in a sample, wherein the presence of the substance is indicative of a disease, infection, or environmental exposure. In some instances, a biomarker can be indicative of how a subject will respond to a particular treatment The term "sample" refers to any biological substance. In some instances, the sample can be a human sample. For example, human samples can be but are not limited to, urine, blood, plasma, saliva, sweat, feces, mucus, semen, vaginal fluids, ocular fluids, cells, cell lysates, proteins, DNA, RNA, metabolites, or tissue. In some instances, the biological sample can be an environmental sample. For example, environmental samples can be but are not limited, soil, water, particulates in the air, and food.

The term "hydrophobic" refers to a material, such as an aerogel, that does not absorb water.

The term "hydrophilic" refers to a material, such as an aerogel, that wicks water into the material, such as an aerogel.

B. Aerogels

Disclosed herein is an air-dried aerogel, such as a resorcinol formaldehyde low density aerogel. The aerogel can have a broad range of pore sizes, such as, for example, from a few nanometers to several microns. The surface characteristics of the aerogel can be modified to make the material highly hydrophilic or hydrophobic. In one aspect, the aerogel can be modified in dried form. In one aspect, the aerogel can be lyophilic. The aerogel disclosed herein can be wet and re-dried while retaining its structure, volume, and integrity. The disclosed aerogel can be used in several devices, including a medical device, a thermoelectric device, an acoustic device, a thermal protection device, in aerospace structures, a water purification device, a chemical separation device, an electrical device, or other specialized applications.

The disclosed aerogels can be made in and can have the same density range as prior resorcinol-formaldehyde aerogels (~100 mg/cc) and can be carbonized in a similar fashion to conventional aerogels. Conventional aerogels requires washing with an organic solvent and supercritical drying. However, researchers have attempted to develop air-drying routes, however organic washing to prevent densification prior to drying is still commonly required in these processes. Contrary to conventional aerogels, the disclosed aerogels can be made a gas-dried solid with very little shrinkage (i.e. reduction of volume) directly with no washing step. As such, the disclosed aerogel can be wet multiple times it's mass with water or oil without changing shape or losing integrity.

With a polar liquid, such as water, several wetting and drying cycles can be performed on the same specimen. The conventional super critically-dried aerogels will wet with water, but they fall apart upon drying after wetting. The disclosed aerogel's unique wetting ability can allow it to be modified after drying for use in many applications that would cause state of the art aerogels to fail—for example, be coated for thermal protection systems, modified for carbon capture systems, modified for specific water remediation systems, coated for incorporation into thermo-electric generators, or utilized in cell scaffolding systems.

Accordingly, disclosed herein is an aerogel comprising a polyhydroxy benzene compound crosslinked with formaldehyde, wherein the aerogel is dry and has a first volume, wherein the aerogel can be exposed to a liquid and be re-dried in a gas while retaining at least 70% of the first volume.

In one aspect, the polyhydroxy benzene compound is a dihydroxy benzene compound. In another aspect, the dihydroxy benzene compound is selected from the group consisting of resorcinol and catechol or a combination thereof. For example, the dihydroxy benzene compound can be resorcinol. In another example, the dihydroxy benzene compound can be catechol.

In one aspect, the molar ratio of the polyhydroxy benzene compound to formaldehyde in the aerogel is from about 1:1 to about 1:4. For example, the molar ratio of the polyhydroxy benzene compound to formaldehyde in the aerogel is from about 1:1 to about 1:3. In another example, the molar ratio of the polyhydroxy benzene compound to formaldehyde in the aerogel is from about 1:1.5 to about 1:2.5. In yet another example, the molar ratio of the polyhydroxy benzene compound to formaldehyde in the aerogel is about 1:2.

In one aspect, the molar ratio of the resorcinol to formaldehyde in the aerogel is from about 1:1 to about 1:4. For example, the molar ratio of the resorcinol to formaldehyde in the aerogel is from about 1:1 to about 1:3. In another example, the molar ratio of the resorcinol to formaldehyde in the aerogel is from about 1:1.5 to about 1:2.5. In yet another example, the molar ratio of the resorcinol to formaldehyde in the aerogel is about 1:2.

The aerogel disclosed herein does not suffer the catastrophic failure when exposed to a liquid and re-dried in a gas, such as air or inert gas, like conventional aerogels. Accordingly, the aerogel can be wet and re-dried in a gas, such as air or inert gas, at least 1, 2, 3, 5, 10, 20, 30, 50, 75, or 100 times while retaining its volume. For example, the aerogel can be wet and re-dried in a gas, such as air or inert gas, from 1 to 100 while retaining its volume. In one aspect, the aerogel has been wet and re-dried in a gas, such as air or inert gas, at least 1, 2, 3, 5, 10, 20, 30, 50, 75, or 100 times while retaining its volume. For example, in some aspects, the aerogel has been wet and re-dried in a gas, such as air or inert gas, from 1 to 100 while retaining its volume. In one aspect, the aerogel can be wet with a polar liquid and be re-dried. Examples of suitable polar liquids include, but are not limited to, water, alcohols, such as methanol, ethanol, propanol, acetic acid, ammonia, acetonitrile, dimethyl sulfoxide, or N,N,-diformamide. The polar liquid, in one aspect, can be water. In another aspect, the aerogel can be wet with a non-polar liquid and be re-dried. Examples of suitable non-polar liquids include, but are not limited to, oils, pentane, hexane, cyclohexane, benzene, toluene, chloroform, diethyl ether. The non-polar liquid, in one aspect, can be an oil.

In one aspect, the aerogel can be exposed to a liquid and be re-dried in a gas while retaining at least 75% of the first volume. In another aspect, the aerogel can be exposed to a liquid and be re-dried in a gas while retaining at least 80% of the first volume. In yet another aspect, the aerogel can be exposed to a liquid and be re-dried in a gas while retaining at least 85% of the first volume. In yet another aspect, the aerogel can be exposed to a liquid and be re-dried in a gas while retaining at least 90% of the first volume. In yet another aspect, the aerogel can be exposed to a liquid and be re-dried in a gas while retaining at least 95% of the first volume. In yet another aspect, the aerogel can be exposed to a liquid and be re-dried in a gas while retaining at least 97% of the first volume. In yet another aspect, the aerogel can be exposed to a liquid and be re-dried in a gas while retaining at least 98% of the first volume. In yet another aspect, the aerogel can be exposed to a liquid and be re-dried in a gas while retaining at least 99% of the first volume. In yet another aspect, the aerogel can be exposed to a liquid and be re-dried in a gas while retaining at least 99.9% of the first volume.

In one aspect, the aerogel is a functionalized aerogel. A functionalized aerogel is an aerogel that has been chemically modified from its original form. For example, the hydroxyl groups (—OH) on the aerogel can be used to bond a chemical linker to the aerogel to produce a functionalized aerogel. For example, an acyl halide moiety on a chemical linker can be reacted with a hydroxyl group on the aerogel to form an ester bond to bond the chemical linker to the aerogel.

In one aspect, the chemical linker modifies the surface properties of the hydrogel. For example, a hydrophilic aerogel can be modified to become hydrophobic by using an alkane type chemical linker. In another aspect, the chemical linker comprises a reactive moiety. The reactive moiety can be used to bond other molecules to the linker and in turn to the aerogel. For example, the chemical linker can comprise an amine, an amide, a silane, an azide, an alkane, an alkene, an alkyne, or a thiol. The amine, amide, silane, azide, alkane, alkene, alkyne, or thiol can be used to attach bond other molecules to the linker and in turn to the aerogel. For example, the linker can be an amine, which can be used for carbon capture applications. In another example, the linker can be a silane, which can be used for hydrophobic application. Silanes can also be used to convert the aerogel to a ceramic material. In yet another example, the chemical linker can be an alkyne, which can be used in life science applications. In one aspect, the chemical linker is or is bonded to a polymer. In one aspect, the linker comprises an azide that can be used to bond a signaling moiety. Thus, in one aspect, the functionalized aerogel comprises the aerogel, a chemical linker, and a signaling moiety, wherein the chemical linker is bound to both the signaling moiety and the aerogel.

As such, the aerogels can be modified for a particular purpose. For example, the aerogel can be modified with a chemical linker comprising a thiol moiety if gold is to be attached to the aerogel. In another example, the aerogel can be modified with an alkyl group if a hydrophobic aerogel is desired. In other application, it may be desired to not modify the aerogel to retain the hydrophobicity and absorptive capabilities of the aerogel, for example, in a medical device to absorb bodily fluids, such as blood, from a wound.

In one aspect, the signaling moiety comprises a detection portion and a target binding portion. In one aspect, a detection portion allows for the aerogel or a portion of the aerogel to be detected. In one aspect, the signaling moiety, in particular the detection portion, can comprise a fluorescent moieties, colloidal gold, enzymes, dyes, radioisotopes, or chemiluminescent markers For example, the detection portion can comprise fluorescence resonance energy transfer (FRET). In one aspect, a target binding portion allows for binding of the signaling moiety to a target, or a specific molecule, in a sample. In one aspect, a target binding portion comprises a RNA molecule, a DNA molecule, an antibody or fragment thereof, or known receptors to biomarkers.

In one aspect, the aerogel is carbonized. The aerogel can be carbonized by conventional methods at elevated temperatures. A carbonized aerogel is suitable for use in electrical devices, for example capacitance devices, and thermal devices. The carbonized aerogel can also be suitable for water treatment applications due to the large surface area for microorganism adsorption or preferential absorption devices. The carbonization of aerogels is described by Tamon et al. *Carbon*, Vol. 36, No. 9, pp 1257-1262 (1998), which is incorporated herein by reference, particularly for its disclosure of carbonization of aerogels.

In one aspect, the aerogel is capable of absorbing up to ten times its mass of a polar liquid or a non-polar liquid. For example, the aerogel is capable of absorbing from six times to ten times its mass of a polar liquid or a non-polar liquid. In another example, the aerogel is capable of absorbing from seven times to ten times its mass of a polar liquid or a non-polar liquid. In another example, the aerogel is capable of absorbing from eight times to ten times its mass of a polar liquid or a non-polar liquid. In yet another example, the aerogel is capable of absorbing from nine times to ten times its mass of a polar liquid or a non-polar liquid. In yet another example, the aerogel is capable of absorbing ten times its mass of a polar liquid or a non-polar liquid. Examples of suitable polar liquids include, but are not limited to, water, alcohols, such as methanol, ethanol, propanol, acetic acid, ammonia, acetonitrile, dimethyl sulfoxide, or N,N,-diformamide. The polar liquid, in one aspect, can be water. In another aspect, the aerogel can be wet with a non-polar liquid and be re-dried. Examples of suitable non-polar liquids include, but are not limited to, oils, pentane, hexane, cyclohexane, benzene, toluene, chloroform, diethyl ether. The non-polar liquid, in one aspect, can be an oil.

C. Method of Making Aerogels

Also disclosed herein are methods of making the disclosed aerogels. Also disclosed herein are aerogels made by the method disclosed herein.

The aerogels disclosed herein can be made by crosslinking polyhydroxy benzene compound with formaldehyde in the presence of an aluminum catalyst. The crosslinking can take place in a degassed and deionized water solution. The aerogel is then dried in gas, such as for example, air or inert gas. The use of an aluminum catalyst produces the aerogels disclosed herein with the desired properties not achieved in conventional aerogels made by conventional methods.

Accordingly, disclosed herein is a method of making an aerogel comprising the steps of: a) crosslinking a polyhydroxy benzene compound with formaldehyde in the presence of an aluminum catalyst, thereby forming a gel having a first volume; and b) drying the gel in gas, thereby forming an aerogel having a second volume.

In one aspect, the step of crosslinking a polyhydroxy benzene compound with formaldehyde in the presence of an aluminum catalyst, thereby forming a gel having a first volume can be performed in a water solution. The water solution can be a degassed and deionized water solution.

In one aspect, the method further comprises further comprises the step of modifying the aerogel with a chemical linker disclosed herein.

Also disclosed herein is a method comprising the steps of: a) providing an aerogel produced by a method disclosed herein; and b) modifying the aerogel with a chemical linker disclosed herein.

The modifying step of the aerogel can be performed when the aerogel is in a solid dry form. In one aspect, an acyl halide group on the chemical linker is reacted with an hydroxyl group on the aerogel to bind the chemical linker to the aerogel via an ester group.

In one aspect, the gas is air. In another aspect, the gas is an inert gas. Suitable inert gases include, but are not limited to, nitrogen and argon.

In one aspect, the step of drying the gel in gas comprises exposing the gel to air having a temperature from about 70° C. to about 120° C. In another aspect, the step of drying the gel in gas comprises exposing the gel to gas having a temperature from about 70° C. to about 100° C. In yet another aspect, the step of drying the gel in gas comprises exposing the gel to gas having a temperature from about 80° C. to about 90° C.

In one aspect, the drying step is performed for at least 6 hours, 12 hours, 1 day, 3 days, 5 days, 7 days, 10 days, or 20 days. For example, the drying step can be performed from 6 hours to 20 days, for example, from 1 day to 10 days.

Thus, for example, the step of drying the gel in gas comprises exposing the gel to air having a temperature from about 70° C. to about 120° C. from 6 hours to 10 days.

In one aspect, the polyhydroxy benzene compound is a dihydroxy benzene compound. In another aspect, the dihydroxy benzene compound is selected from the group consisting of resorcinol and catechol or a combination thereof. For example, the dihydroxy benzene compound can be resorcinol. In another example, the dihydroxy benzene compound can be catechol.

In one aspect, the second volume is at least 70% of the first volume. In another aspect, the second volume is at least 80% of the first volume. In yet another aspect, the second volume is at least 85% of the first volume. In yet another aspect, the second volume is at least 90% of the first volume. In yet another aspect, the second volume is at least 95% of the first volume. In yet another aspect, the second volume is at least 97% of the first volume. In yet another aspect, the second volume is at least 98% of the first volume. In yet another aspect, the second volume is at least 99% of the first volume. In yet another aspect, the second volume is at least 99.9% of the first volume.

The aluminum catalyst can be in the form of an aluminum salt or aluminum produced from an aluminum electrode. Accordingly, in one aspect, the aluminum catalyst comprises an aluminum salt catalyst. Suitable aluminum salts include, but are not limited to aluminum acetate, aluminum citrate, aluminum chloride, or aluminum oxide or a combination thereof. For example, the aluminum salt can comprise aluminum acetate.

In one aspect, aluminum catalyst can be mixed with a sodium catalyst, such as a sodium salt. Suitable sodium catalysts, such as sodium salts, that can be mixed with the aluminum catalyst include, but are not limited to sodium acetate, sodium hydroxide, sodium tetraborate, and sodium lingosulfonate.

In another aspect, the aluminum catalyst is aluminum produced from an aluminum electrode at a voltage. In one aspect, the aluminum catalyst is aluminum produced from an aluminum electrode at a voltage from 20V to 100V. For example, the aluminum catalyst can aluminum produced from an aluminum electrode at a voltage from 20V to 80V. In another example, the aluminum catalyst can aluminum produced from an aluminum electrode at a voltage from 20V to 60V.

The crosslinking of the polyhydroxy benzene compound with formaldehyde can take place in a solvent. The solvent can have a pH that is neutral or acidic. In one aspect, the crosslinking of the polyhydroxy benzene compound with formaldehyde can take place in a solvent having a pH of about 3 to about 7. In another aspect, the crosslinking of the polyhydroxy benzene compound with formaldehyde can take place in a solvent having a pH of about 4 to about 6. In yet another aspect, the solvent can have a pH that is basic. In yet another aspect, the crosslinking of the polyhydroxy benzene compound with formaldehyde can take place in a solvent having a pH of about 7 to about 12.

The solvent of the crosslinking can be a polar solvent. In one aspect, the solvent of the crosslinking comprises water.

The polyhydroxy benzene compound and formaldehyde can be mixed at various ratios. In one aspect, the molar ratio of the polyhydroxy benzene compound to formaldehyde in the crosslinking step is from about 1:1 to about 1:4. In another aspect, the molar ratio of the polyhydroxy benzene compound to formaldehyde in the crosslinking step is from about 1:1 to about 1:3. In yet another aspect, the molar ratio of the polyhydroxy benzene compound to formaldehyde in the crosslinking step is from about 1:1.5 to about 1:2.5.

D. Methods of Detecting a Biological Condition

Disclosed are methods of detecting a biological condition in a subject using any of the disclosed aerogels. A biological condition, as described herein, refers to any condition that has a circulating or detectable biomarker. In some instances, a biological condition can be a disease, a disorder, an infection, or an environmental exposure. Biological conditions can be brought about by environmental factors, genetic factors, or a combination thereof. Examples of environmental factors can be, but are not limited to, air and water pollutants, metal toxicity, radiation, stress, temperature, or infectious agents. In some instances, a biological condition can be, but is not limited to, radiation sickness, heavy metal poisoning, cancer, autoimmune disorders, embryological or developmental disorders, parasitic infection, viral infection, or bacterial infection. Circulating or detectable biomarkers can be, but are not limited to, nucleic acids, proteins, metals, metabolites, or a combination thereof. For example, if the biological condition is radiation exposure, biomarkers can be, but are not limited to, amylase, diamine oxidase, Flt3L, citrulline, gamma-H2AX, p53, TRAIL receptor 2, FHL2, cyclin G, cyclin protein gene, or a combination thereof. If the biological condition is a viral infection, biomarkers can be, but are not limited to, myxovirus resistance A (MxA), C-reactive protein (CRP), cytokines, chemokines, specific miRNAs or a combination thereof.

Disclosed are methods comprising incubating a sample obtained from a subject with an aerogel comprising a polyhydroxy benzene compound crosslinked with formaldehyde, wherein the aerogel is dry and has a first volume, wherein the aerogel can be exposed to a liquid and be re-dried in a gas while retaining at least 70% of the first volume, wherein the aerogel is a functionalized aerogel, wherein the functionalized aerogel comprises the aerogel, a chemical linker, and a signaling moiety, wherein the chemical linker is bound to both the signaling moiety and the aerogel, wherein the signaling moiety comprises a detection portion and a target binding portion, and determining the presence or absence of a biomarker for a biological condition in the sample using the signaling moiety of the aerogel, wherein the presence of the biomarker indicates the subject has a biological condition, wherein the absence of the biomarker indicates the subject does not have a biological condition.

Disclosed are methods comprising incubating a sample obtained from a subject with an aerogel comprising a polyhydroxy benzene compound crosslinked with formaldehyde, wherein the aerogel is dry and has a first volume, wherein the aerogel can be exposed to a liquid and be re-dried in a gas while retaining at least 70% of the first volume, wherein the aerogel is a functionalized aerogel, wherein the functionalized aerogel comprises the aerogel, a chemical linker, and a signaling moiety, wherein the chemical linker is bound to both the signaling moiety and the aerogel, wherein the signaling moiety comprises a detection portion and a target binding portion, and determining the presence or absence of a biomarker for a biological condition in the sample using the signaling moiety of the aerogel, wherein the presence of the biomarker indicates the subject has a biological condition, wherein the absence of the biomarker indicates the subject does not have a biological condition, wherein the signaling moiety provides a positive signal in the presence of the biomarker. In some instances, the positive signal can be a fluorescent signal. In some instance, a positive signal is determined by running a control wherein there is no sample added and therefore there is no biomarker present to bind to the target binding portion. If the sample provides a signal that is higher than or more than that seen in the control then there is a positive signal and there was biomarker present in the sample.

Disclosed are methods comprising incubating a sample obtained from a subject with an aerogel comprising a polyhydroxy benzene compound crosslinked with formaldehyde, wherein the aerogel is dry and has a first volume, wherein the aerogel can be exposed to a liquid and be re-dried in a gas while retaining at least 70% of the first volume, wherein the aerogel is a functionalized aerogel, wherein the functionalized aerogel comprises the aerogel, a chemical linker, and a signaling moiety, wherein the chemical linker is bound to both the signaling moiety and the aerogel, wherein the signaling moiety comprises a detection portion and a target binding portion, and determining the presence or absence of a biomarker for a biological condition in the sample using the signaling moiety of the aerogel, wherein the presence of the biomarker indicates the subject has a biological condition, wherein the absence of the biomarker indicates the subject does not have a biological condition, wherein the biomarker is a nucleic acid, protein or metal. In some instances, a nucleic acid can be miRNA. In some instances, a nucleic acid can be DNA.

Disclosed are methods comprising incubating a sample obtained from a subject with an aerogel comprising a polyhydroxy benzene compound crosslinked with formaldehyde, wherein the aerogel is dry and has a first volume, wherein the aerogel can be exposed to a liquid and be re-dried in a gas while retaining at least 70% of the first volume, wherein the aerogel is a functionalized aerogel, wherein the functionalized aerogel comprises the aerogel, a chemical linker, and a signaling moiety, wherein the chemical linker is bound to both the signaling moiety and the aerogel, wherein the signaling moiety comprises a detection portion and a target binding portion, and determining the presence or absence of a biomarker for a biological condition in the sample using the signaling moiety of the aerogel, wherein the presence of the biomarker indicates the subject has a biological condition, wherein the absence of the biomarker indicates the subject does not have a biological condition, wherein the target binding portion binds to the biomarker. A target binding portion can be anything that binds to a biomarker. For example, a target binding portion can be, but is not limited to, a nucleic acid, protein, or metal chelators (e.g. EDTA). In some instances, a target binding portion comprises a RNA molecule, a DNA molecule, an antibody or fragment thereof, anti-microbial peptides such as cathelicidins, charged metals such as nickel (binds to Histadine residues on proteins) or iron (binds to proteins with heme-components) or known receptors to biomarkers.

Disclosed are methods comprising incubating a sample obtained from a subject with an aerogel comprising a polyhydroxy benzene compound crosslinked with formaldehyde, wherein the aerogel is dry and has a first volume, wherein the aerogel can be exposed to a liquid and be re-dried in a gas while retaining at least 70% of the first volume, wherein the aerogel is a functionalized aerogel, wherein the functionalized aerogel comprises the aerogel, a chemical linker, and a signaling moiety, wherein the chemical linker is bound to both the signaling moiety and the aerogel, wherein the signaling moiety comprises a detection portion and a target binding portion, and determining the presence or absence of a biomarker for a biological condition in the sample using the signaling moiety of the aerogel, wherein the presence of the biomarker indicates the subject has a biological condition, wherein the absence of the biomarker indicates the subject does not have a biological condition, wherein the biological condition is an infectious disease, autoimmune disease, radiation exposure, or a genetic disorder.

Disclosed are methods comprising incubating a sample obtained from a subject with an aerogel comprising a polyhydroxy benzene compound crosslinked with formaldehyde, wherein the aerogel is dry and has a first volume, wherein the aerogel can be exposed to a liquid and be re-dried in a gas while retaining at least 70% of the first volume, wherein the aerogel is a functionalized aerogel, wherein the functionalized aerogel comprises the aerogel, a chemical linker, and a signaling moiety, wherein the chemical linker is bound to both the signaling moiety and the aerogel, wherein the signaling moiety comprises a detection portion and a target binding portion, and determining the presence or absence of a biomarker for a biological condition in the sample using the signaling moiety of the aerogel, wherein the presence of the biomarker indicates the subject has a biological condition, wherein the absence of the biomarker indicates the subject does not have a biological condition, wherein the sample is blood.

E. Method of Detecting a Biomarker

Disclosed are methods of detecting a biomarker for a biological condition in the sample using the aerogels disclosed above.

Disclosed are methods of detecting comprising the steps of incubating a sample with an aerogel comprising a polyhydroxy benzene compound crosslinked with formaldehyde, wherein the aerogel is dry and has a first volume, wherein the aerogel can be exposed to a liquid and be re-dried in a gas while retaining at least 70% of the first volume, wherein the aerogel is a functionalized aerogel, wherein the functionalized aerogel comprises the aerogel, a chemical linker, and a signaling moiety, wherein the chemical linker is bound to both the signaling moiety and the aerogel, wherein the signaling moiety comprises a detection portion and a target binding portion, and detecting the presence or absence of a biomarker for a biological condition in the sample using the signaling moiety of the aerogel. The signaling moiety is a moiety that can be detected directly or indirectly. For example, a signaling moiety, specifically the detection portion, can be, but is not limited to, colorimetric indicators, fluorescent moieties, colloidal gold, enzymes, dyes, detection by refractive index, radioisotopes, or chemiluminescent markers. In some instances, direct detection of a signaling moiety can occur when the binding of the biomarker to the target binding portion triggers a reaction that causes the detection portion to be detected. For example, binding of the biomarker to the target binding portion can change the conformation of the detection portion which allows for the detection portion to emit a signal and be detected. In some instances, indirect detection of a signaling moiety occurs when the detection portion requires something other than simply the binding of the biomarker to the target binding portion in order for the detection portion to be detected. For example, binding of the biomarker to the target binding portion can result in a conformational change of the detection portion which can then be bound by a labeled antibody that binds only to the new conformational shape wherein the labeled antibody bound to the detection portion can be detected.

Disclosed are methods of detecting comprising the steps of incubating a sample with an aerogel comprising a polyhydroxy benzene compound crosslinked with formaldehyde, wherein the aerogel is dry and has a first volume, wherein the aerogel can be exposed to a liquid and be re-dried in a gas while retaining at least 70% of the first volume, wherein the aerogel is a functionalized aerogel, wherein the functionalized aerogel comprises the aerogel, a chemical linker, and a signaling moiety, wherein the chemical linker is bound to both the signaling moiety and the aerogel, and detecting the presence or absence of a biomarker for a biological condition in the sample using the signaling moiety of the aerogel, wherein detecting the presence of the biomarker comprises a positive signal provided from the signaling moiety of the aerogel. In some instance, a positive signal is determined by running a control wherein there is no sample added and therefore there is no biomarker present to bind to the target binding portion. If the sample provides a signal that is higher than or more than that seen in the control then there is a positive signal and there was biomarker present in the sample.

Disclosed are methods of detecting comprising the steps of incubating a sample with an aerogel comprising a polyhydroxy benzene compound crosslinked with formaldehyde, wherein the aerogel is dry and has a first volume, wherein the aerogel can be exposed to a liquid and be re-dried in a gas while retaining at least 70% of the first volume, wherein the aerogel is a functionalized aerogel, wherein the functionalized aerogel comprises the aerogel, a chemical linker, and a signaling moiety, wherein the chemical linker is bound to both the signaling moiety and the aerogel, and detecting the presence or absence of a biomarker for a biological condition in the sample using the signaling moiety of the aerogel, wherein detecting the absence of the biomarker comprises a negative signal or lack of signal provided from the signaling moiety of the aerogel. In some instance, a negative signal or lack of signal is determined by running a control wherein there is no sample added and therefore there is no biomarker present to bind to the target binding portion. The control would result in a negative signal or lack of signal. Thus, if the sample is the same as the control, then there was no biomarker present in the sample.

Disclosed are methods of detecting comprising the steps of incubating a sample with an aerogel comprising a polyhydroxy benzene compound crosslinked with formaldehyde, wherein the aerogel is dry and has a first volume, wherein the aerogel can be exposed to a liquid and be re-dried in a gas while retaining at least 70% of the first volume, wherein the aerogel is a functionalized aerogel, wherein the functionalized aerogel comprises the aerogel, a chemical linker, and a signaling moiety, wherein the chemical linker is bound to both the signaling moiety and the aerogel, and detecting the presence or absence of a biomarker for a biological condition in the sample using the signaling moiety of the aerogel, wherein the sample is blood.

Disclosed are methods of detecting comprising the steps of incubating a sample with an aerogel comprising a polyhydroxy benzene compound crosslinked with formaldehyde, wherein the aerogel is dry and has a first volume, wherein the aerogel can be exposed to a liquid and be re-dried in a gas while retaining at least 70% of the first volume, wherein the aerogel is a functionalized aerogel, wherein the functionalized aerogel comprises the aerogel, a chemical linker, and a signaling moiety, wherein the chemical linker is bound to both the signaling moiety and the aerogel, and detecting the presence or absence of a biomarker for a biological condition in the sample using the signaling moiety of the aerogel, wherein the biomarker is a nucleic acid, protein or metal. In some instances, a nucleic acid can be miRNA. In some instances, a nucleic acid can be DNA.

F. Uses

Also disclosed herein are methods of using the aerogel disclosed herein. In one aspect, the aerogel can be a hydrophilic aerogel. The hydrophilic aerogel can be applied to a wound of a subject, wherein the hydrophilic aerogel absorbs bodily fluids, such as blood and/or pus, from the wound.

In another aspect, the aerogel can be carbonized and can be applied in an electrical device that performs as a capacitor.

In another aspect, the aerogel can be modified for applications in thermal or acoustic applications, such as, for example, insulation from heat or noise.

In yet another aspect, the aerogel can be carbonized and placed in a water treatment system. Microorganism can adsorb to the carbonized aerogel, which has a high surface area, and promote water treatment. Organic material in the water can also be adsorbed onto the carbonized aerogel.

In another aspect, the aerogel, due to its 3D nature, can be used to recreate a 3D environment to study cellular physiology in mixed cell cultures. This system can be used for basic research, manufacturing, processing or implantation as individual cells, tissues, or whole organs. Cells can be seeded and cultured on the aerogel.

In another aspect, the aerogel can act as a probe to trap to a biomarker. In some instances, it can act as a filter. In some instances, extraneous and non-target biologicals can be retained or filtered through the aerogel based on size and adhesive properties. Because of the signaling moiety (e.g. fluorescent design) of the aerogel, only biological/chemical material (i.e. biomarker of interest) can bind to the probe and can be detected by light excitation.

G. Devices

Also disclosed herein are devices comprising the aerogel disclosed herein. In one aspect, the device comprises a hydrophilic aerogel disclosed herein. In another aspect, the device comprises a hydrophobic aerogel disclosed herein. In yet another aspect, the device comprises a carbonized aerogel disclosed herein. In yet another aspect, the device comprises a functionalized aerogel disclosed herein.

In one aspect, the device is a medical device. The medical device can be used to absorb absorbs bodily fluids, such as blood and/or pus, from the wound. Thus, for example, the device can be a wound dressing. The aerogel, in these aspects, can be a hydrophilic aerogel.

In one aspect, the device can be a three dimensional porous structure to which cells are seeded and cultured to facilitate a three dimensional structure while allowing for media stay in contact with, and prevent general necrosis of, the cultured cells. This device could be coated with signaling molecules using linking chemistry.

In one aspect, the device can be a water purification device. In one example, the water purification device can be a water treatment plant. In another example, water purification device can comprise a container, such as, for example a bottle. The water purification device can, in these aspects, can be configured to filter or contact water prior to use by a consumer. The aerogel, in these aspects, can be a carbonized aerogel. Thus, in one aspect, the device is a membrane distillation device.

In one aspect, the device can be a chemical separation device. The device and aerogel can be configured to allow for selective adsorption or absorption of chemicals into the aerogel. The chemical can also, in some aspects, bind to the aerogel. The adsorption and or absorption of selected chemicals allows for chemical of these chemical from a mixture of chemicals.

In one aspect, the device can be an electrical device. The aerogel, in these aspects, can be a carbonized aerogel. The electrical device can be a capacitor. The electrical device can also be a thermo-electrical device.

In one aspect, the device is a device for insulation, such as thermal or acoustic insulation device. The aerogel can be one or more layers in a multi-layer insulation device.

In one aspect, the device is configured to be used to capture carbon.

Aspects

In view of the disclosure herein below are described certain more particularly described aspects of the inventions. These particularly recited aspects should not however be interpreted to have any limiting effect on any different claims containing different or more general teachings described herein, or that the "particular" aspects are somehow limited in some way other than the inherent meanings of the language and formulas literally used therein.

Aspect 1: An aerogel comprising a polyhydroxy benzene compound crosslinked with formaldehyde, wherein the aerogel is dry and has a first volume, wherein the aerogel can be exposed to a liquid and be re-dried in a gas while retaining at least 70% of the first volume.

Aspect 2: The aerogel of aspect 1, wherein the aerogel is hydrophilic.

Aspect 3: The aerogel of aspect 1, wherein the aerogel is hydrophobic.

Aspect 4: The aerogel of any one of aspects 1-3, wherein the aerogel is a functionalized aerogel.

Aspect 5: The aerogel of aspect 4, wherein the functionalized aerogel comprises the aerogel and a chemical linker.

Aspect 6: The aerogel of aspect 5, wherein the chemical linker comprises an ester or ether bond.

Aspect 7: The aerogel of aspects 5 or 6, wherein the chemical linker comprises a reactive moiety.

Aspect 8: The aerogel of any one of aspects 4-7, wherein the chemical linker comprises an amine, an amide, a silane, an azide, an alkane, an alkene, an alkyne, or a thiol.

Aspect 9: The aerogel of any one of aspects 4-8, wherein the functionalized aerogel comprises the aerogel, a chemical linker, and a signaling moiety, wherein the chemical linker is bound to both the signaling moiety and the aerogel.

Aspect 10: The aerogel of aspect 9, wherein the signaling moiety comprises a detection portion and a target binding portion.

Aspect 11: The aerogel of aspect 10, wherein the detection portion comprises fluorescence resonance energy transfer (FRET).

Aspect 12: The aerogel of any one of aspects 1-11, wherein the polyhydroxy benzene compound is a dihydroxy benzene compound.

Aspect 13: The aerogel of aspect 12, wherein the dihydroxy benzene compound is selected from the group consisting of resorcinol and catechol or a combination thereof.

Aspect 14: The aerogel of aspects 12, wherein the dihydroxy benzene compound is resorcinol.

Aspect 15: The aerogel of any one of aspects 1-14, wherein the molar ratio of the polyhydroxy benzene compound to formaldehyde in the aerogel is from about 1:1 to about 1:4.

Aspect 16: The aerogel of any one of aspects 1-15, wherein the aerogel has been exposed to a liquid and been re-dried in air.

Aspect 17: The aerogel of aspect 16, wherein the liquid is a non-polar liquid.

Aspect 18: The aerogel of aspect 16, wherein the liquid is a polar liquid.

Aspect 19: The aerogel of any one of aspects 1-18, wherein the aerogel can be exposed to a liquid and be re-dried in air while retaining at least 90% of the first volume.

Aspect 20: A method of making an aerogel comprising the steps of: a) crosslinking a polyhydroxy benzene compound with formaldehyde in the presence of an aluminum catalyst, thereby forming a gel having a first volume; and b) drying the gel in gas, thereby forming an aerogel having a second volume.

Aspect 21: The method of aspect 20, wherein the polyhydroxy benzene compound is a dihydroxy benzene compound.

Aspect 22: The method of aspect 21, wherein the dihydroxy benzene compound is selected from the group consisting of resorcinol and catechol or a combination thereof.

Aspect 23: The method of aspect 21, wherein the dihydroxy benzene compound is resorcinol.

Aspect 24: The method of any one of aspects 20-23, wherein the aluminum catalyst is an aluminum salt catalyst.

Aspect 25: The method of aspect 24, wherein the aluminum salt catalyst comprises aluminum acetate, aluminum citrate, aluminum chloride, or aluminum oxide or a combination thereof.

Aspect 26: The method of aspects 24, wherein the aluminum salt catalyst comprises aluminum acetate.

Aspect 27: The method of any one of aspects 20-23, wherein the aluminum catalyst is aluminum produced from an aluminum electrode at a voltage from 20V to 100V.

Aspect 28: The method of any one of aspects 20-27, wherein the second volume of aerogel is at least 70% of the first volume of the gel.

Aspect 29: The method of any one of aspects 20-28, wherein the step of drying the gel in gas comprises exposing the gel to gas having a temperature from about 70° C. to about 120° C.

Aspect 30: The method of any one of aspects 20-29, wherein the step of drying the gel in air comprises exposing the gel to gas having a temperature from about 80° C. to about 90° C.

Aspect 31: The method of any one of aspects 20-30, wherein the crosslinking takes place in a solvent having a pH of from about 3 to about 7.

Aspect 32: The method of any one of aspects 20-31, wherein the crosslinking takes place in a solvent having a pH of from about 4 to about 6.

Aspect 33: The method of aspect 32, wherein the solvent comprises water.

Aspect 34: The method of any one of aspects 20-33, wherein the molar ratio of the polyhydroxy benzene compound to formaldehyde in the crosslinking step is from about 1:1 to about 1:4.

Aspect 35: The method of any one of aspects 20-34, wherein the method further comprises the step of modifying the aerogel with a chemical linker and a signaling moiety.

Aspect 36: The method of aspect 35, wherein the chemical linker is bound to both the signaling moiety and the aerogel.

Aspect 37: The method of aspect 35, wherein the signaling moiety comprises a detection portion and a target binding portion.

Aspect 38: The method of aspect 37, wherein the detection portion comprises fluorescence resonance energy transfer (FRET).

Aspect 39: The method of aspect 37, wherein the target binding portion comprises a RNA molecule that binds to a target.

Aspect 40: An aerogel produced by the method of any one of aspects 20-39.

Aspect 41: The aerogel of aspect 40, wherein the aerogel is capable of absorbing up to ten times its mass of a polar liquid or a non-polar liquid.

Aspect 42: A method comprising the steps of: a) providing the aerogel of any one of aspects 1-19 or 40-41; and b) modifying the aerogel with a chemical linker.

Aspect 43: The method of aspect 42, wherein the chemical linker is further modified with a signaling moiety.

Aspect 44: The method of aspect 43, wherein the chemical linker is bound to both the signaling moiety and the aerogel.

Aspect 45: The method of aspect 43, wherein the signaling moiety comprises a detection portion and a target binding portion Aspect 46: The method of aspect 45, wherein the detection portion comprises fluorescence resonance energy transfer (FRET).

Aspect 47: The method of aspect 45, wherein the target binding portion comprises a RNA molecule that binds to a target.

Aspect 48: A method comprising a) incubating a sample obtained from a subject with the aerogel of any one of aspects 10-19; and b) determining the presence or absence of a biomarker for a biological condition in the sample using the signaling moiety of the aerogel, wherein the presence of the biomarker indicates the subject has a biological condition, wherein the absence of the biomarker indicates the subject does not have a biological condition.

Aspect 49: The method of aspect 48, wherein the signaling moiety provides a positive signal in the presence of the biomarker.

Aspect 50: The method of aspect 49, wherein the positive signal is a fluorescent signal.

Aspect 51: The method of any one of aspects 48-50, wherein the biomarker is a nucleic acid, protein or metal.

Aspect 52: The method of aspects 49, wherein the nucleic acid is miRNA.

Aspect 53: The method of any one of aspects 48-52, wherein the target binding portion binds to the biomarker.

Aspect 54: The method of aspect 53, wherein the target binding portion comprises a RNA molecule.

Aspect 55: The method of any one of aspects 48-54, wherein the biological condition is an infectious disease, autoimmune disease, radiation exposure, or a genetic disorder.

Aspect 56: The method of any one of aspects 48-55, wherein the sample is blood.

Aspect 57: A method of detecting comprising the steps of: a) incubating a sample with the aerogel of aspect 9; and b) detecting the presence or absence of a biomarker for a biological condition in the sample using the signaling moiety of the aerogel.

Aspect 58: The method of aspect 57, wherein detecting the presence of the biomarker comprises a positive signal provided from the signaling moiety of the aerogel.

Aspect 59: The method of aspects 57 or 58, wherein detecting the absence of the biomarker comprises a negative signal or lack of signal provided from the signaling moiety of the aerogel.

Aspect 60: The method of any one of aspects 57-59, wherein the sample is blood.

Aspect 61: The method of any one of aspects 57-60, wherein the biomarker is a nucleic acid, protein or metal.

Aspect 62: The method of aspect 61, wherein the nucleic acid is a miRNA.

Aspect 63: A device comprising the aerogel of any one of aspects 1-19 or 40-41.

Aspect 64: The device of aspect 63, wherein the device is a medical device.

Aspect 65: The device of aspect 63, wherein the device is a water purification device.

Aspect 66: The device of aspect 63, wherein the device is a chemical separation device.

Aspect 67: The device of aspect 63, wherein the device is an electrical device.

Examples

A. Aerogels and Carbon Foams

Four different types of carbon foam were tested C4501, C4502, BQ001, BQ001 hydrophobic. C4501 and C4502 were synthesized with aluminum acetate-deionized water solution that had been allowed to mix for one hour before polyhydroxy benzene and formaldehyde were added, mixed completely and allowed to cure at 90° C. They were then dried before being carbonized in an inert environment at approximately 1050° C. BQ001 was synthesized in a similar manner except the polyhydroxyl benzene-formaldehyde-aluminum acetate-deionized water solution was absorbed into and filled the pore volume of an alumina felt. BQ001 hydrophobic was synthesized in a similar manner to BQ001 except it was rendered hydrophobic after carbonization. All the experiments were performed in a 3-electrode system (FIG. 1), the approximated area of the carbon foams tested were 1.4 $cm^2$.

The first set of experiments consisted in the study of the electrochemical performance of the carbon foams in two different electrolytes: one aqueous (0.5M $H_2SO_4$) and one non-aqueous (1M $LiClO_4$). The advantages of using one versus the other is that an aqueous electrolyte can give higher conductivity and are environmentally friendly; a non-aqueous electrolyte, although it has a lower conductivity, can allow for a wider voltage range for the tests.

Figure 2A:
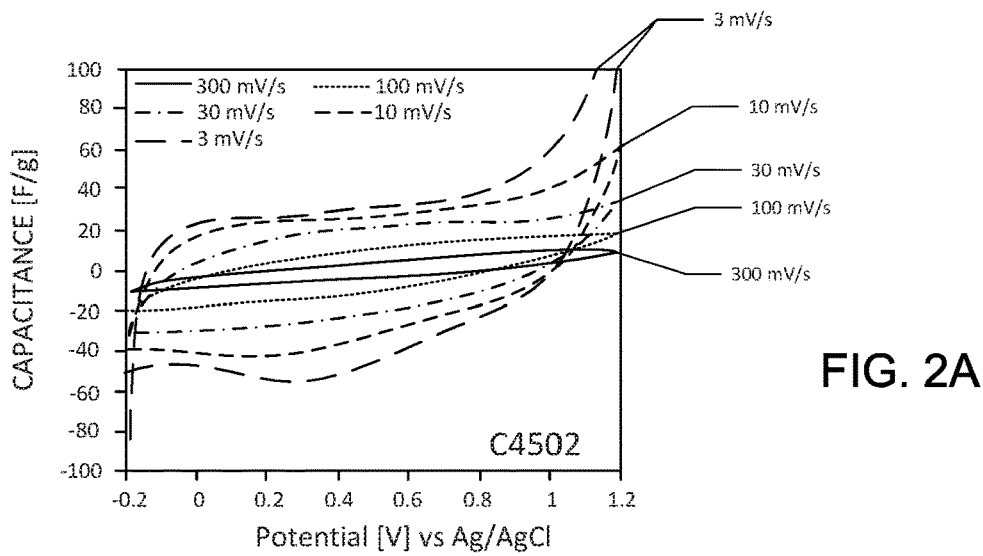
FIGS. 2A, 2B, and 2C show cyclic voltammetry profiles for the three carbon foams (C4502, C4501, and BQ001 respectively) that can be tested in aqueous electrolyte (0.5M $H_2SO_4$).
Figure 2B:
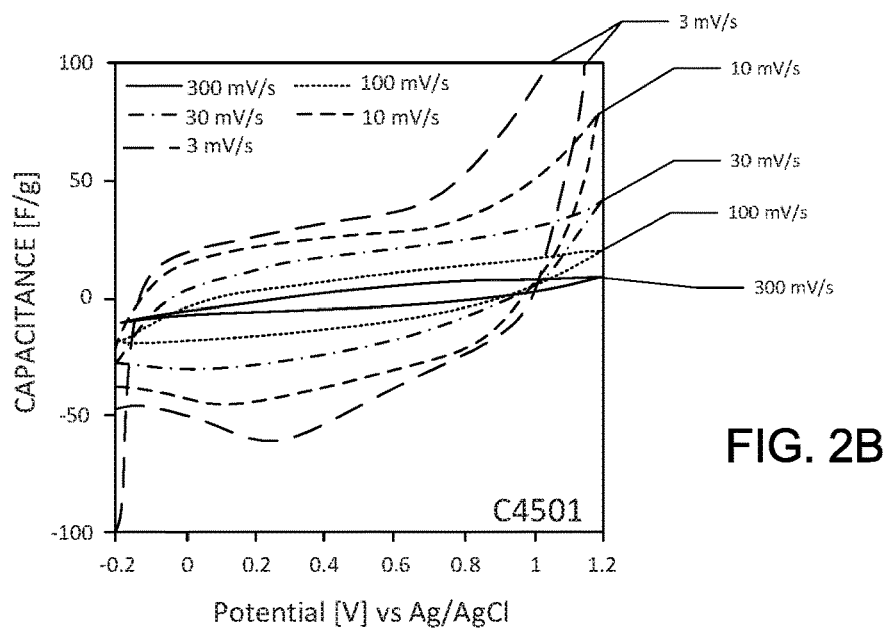
Figure 2C:
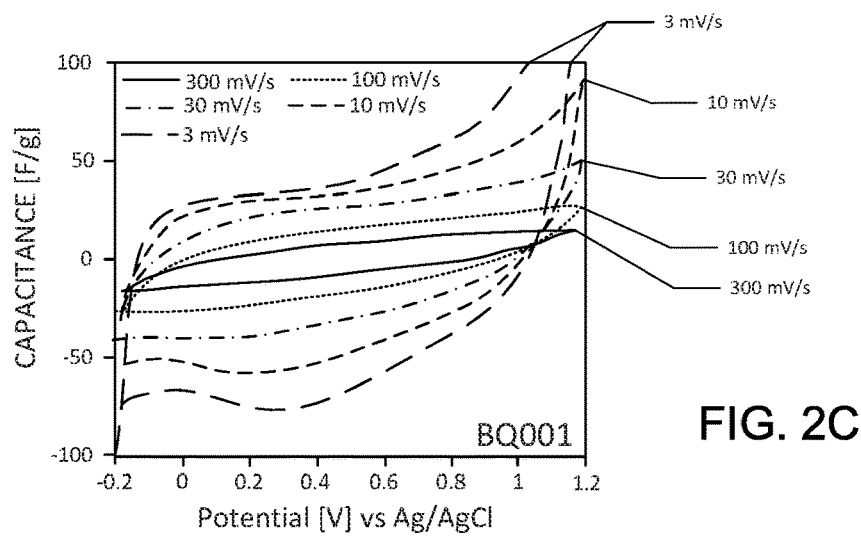

FIGS. 2A, 2B, and 2C show the cyclic voltammetry profiles in terms of capacitance (farads/g) vs. potential at various scan rates, for C4502, C4501 and BQ001 respectively tested in 0.5M $H_2SO_4$. From this test BQ001 is the sample that presents a higher capacitance comparing with C4502 and C4501 that show very similar performance.

Figure 3A:
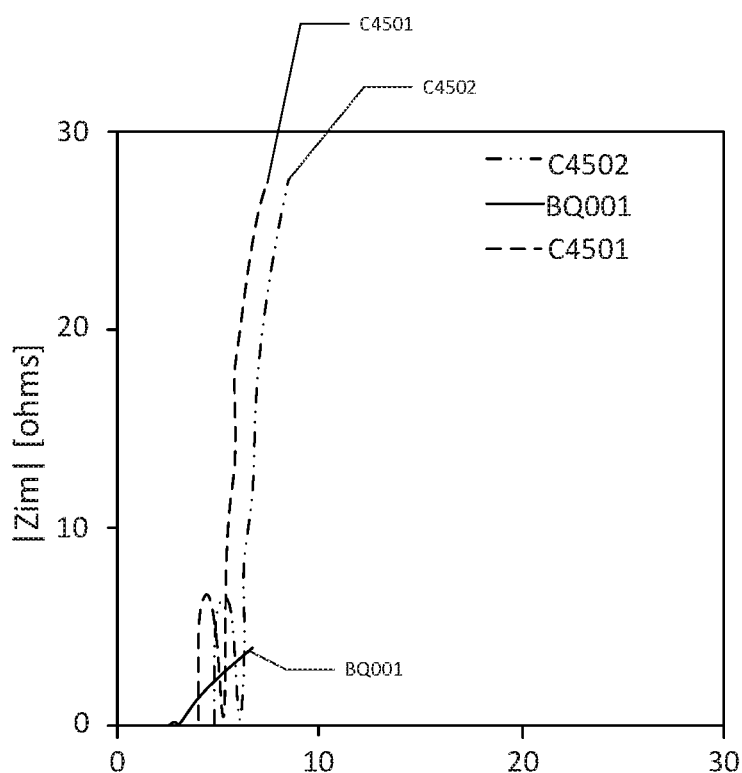
FIG. 3A shows a Nyquist plot from Impedance spectroscopy.
Figure 3B:
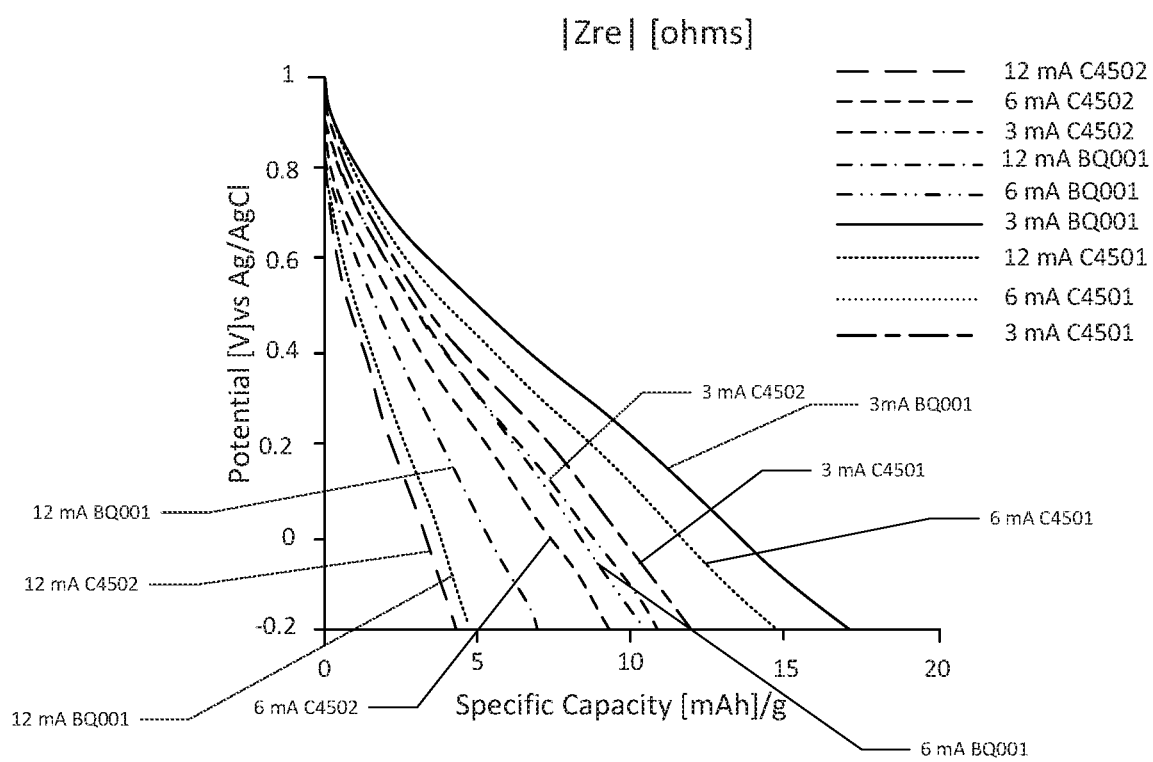
FIG. 3B shows Discharge profiles, Potential vs. Specific Capacity.

FIG. 3a shows the Nyquist plot for real and imaginary impedance of the three samples, C4502 and C4501 present similar resistance, whereas BQ001 presents lower impedance comparing with the other two samples, which indicates this sample has higher conductivity. FIG. 3b shows the discharge profiles normalized to specific capacity (mAh/g), similar to impedance, C4501 and C4502 show similar discharge profiles, while BQ001 has a higher specific capacity (amount of charge that can be stored) when compared to the other two samples.

Figure 4A:
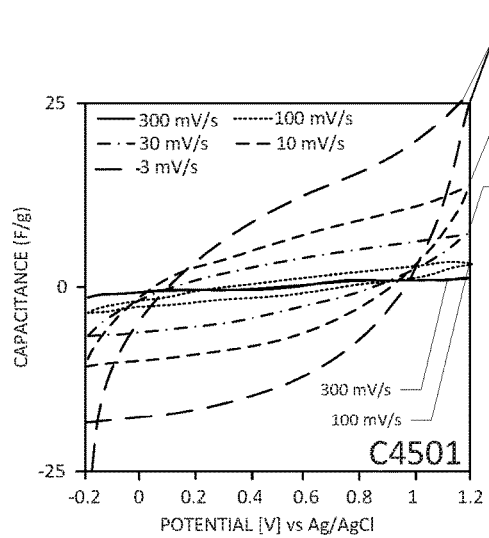
FIGS. 4A, 4B, 4C, and 4D show cyclic voltammetry profiles for the four carbon foams (C4502, C4501, BQ001, and BQ001 hydrophobic respectively) that can be tested in non-aqueous electrolyte (1M $LiClO_4$).
Figure 4B:
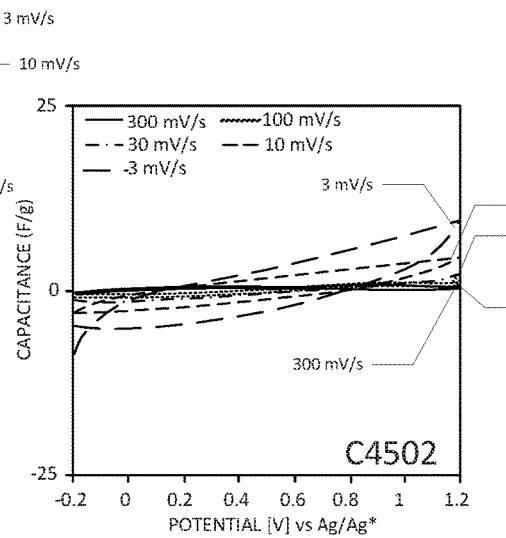
Figure 4C:
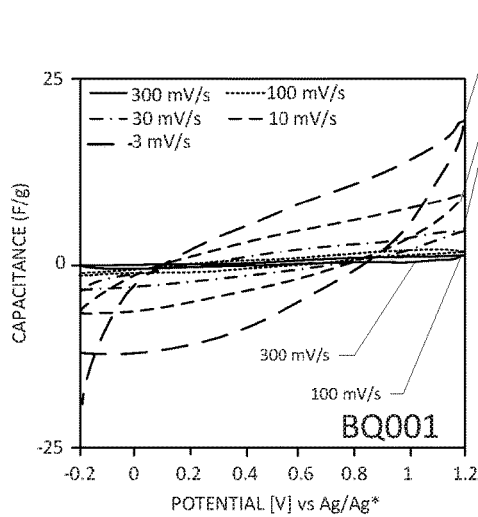
Figure 4D:
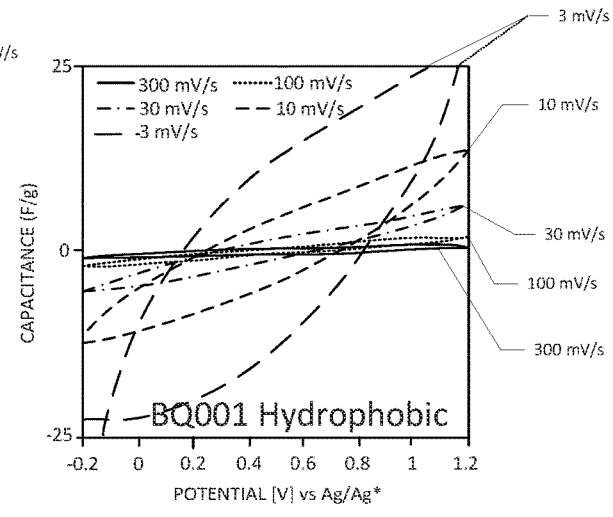
Figure 5A:
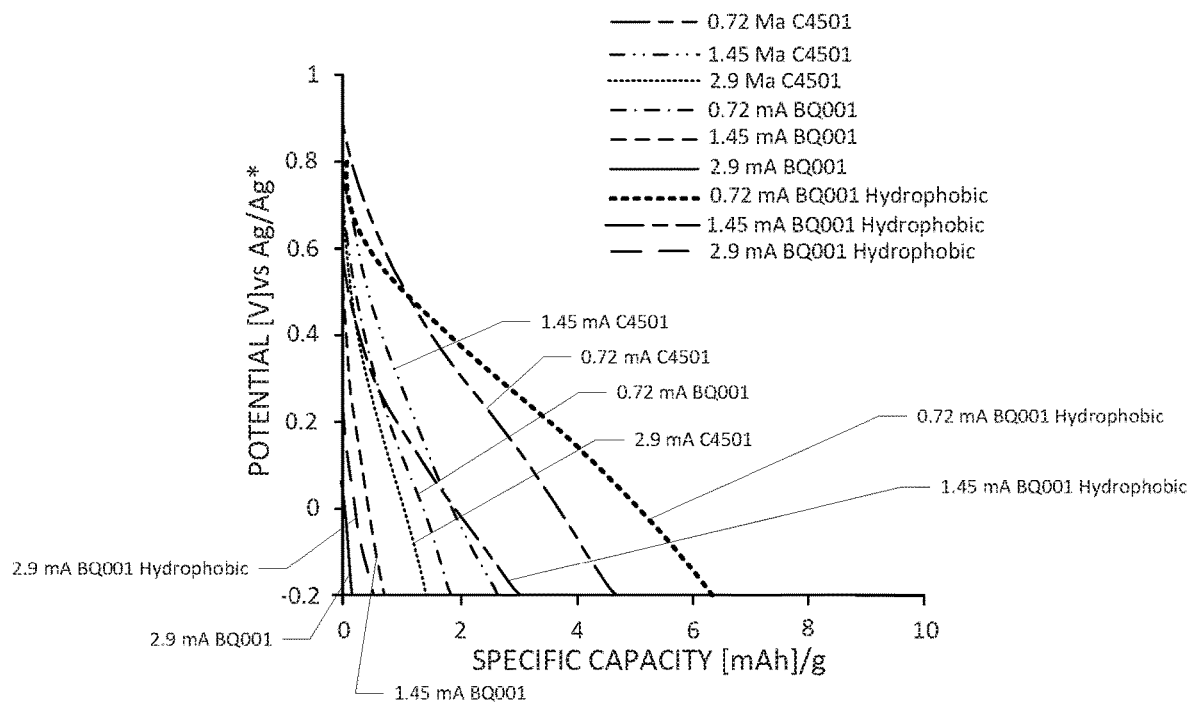
FIG. 5A shows discharge profiles, Potential vs. Specific Capacity of samples C4501, BQ001, BQ001 hydrophobic

FIGS. 4A, 4B, 4C, and 4D show the cyclic voltammetry profiles normalized by the scan rate and the mass (capacitance) of the samples tested in 1M $LiClO_4$ at various scan rates. C4501 and C4502 seem to have different electrochemical performance in non-aqueous electrolyte, where C4501 presents a higher capacitance comparing with C4502. FIG. 5A shows BQ001 hydrophobic shows a better electrochemical behavior than BQ001, although there is more scan rate dependence in BQ001 hydrophobic than BQ001.

Figure 5B:
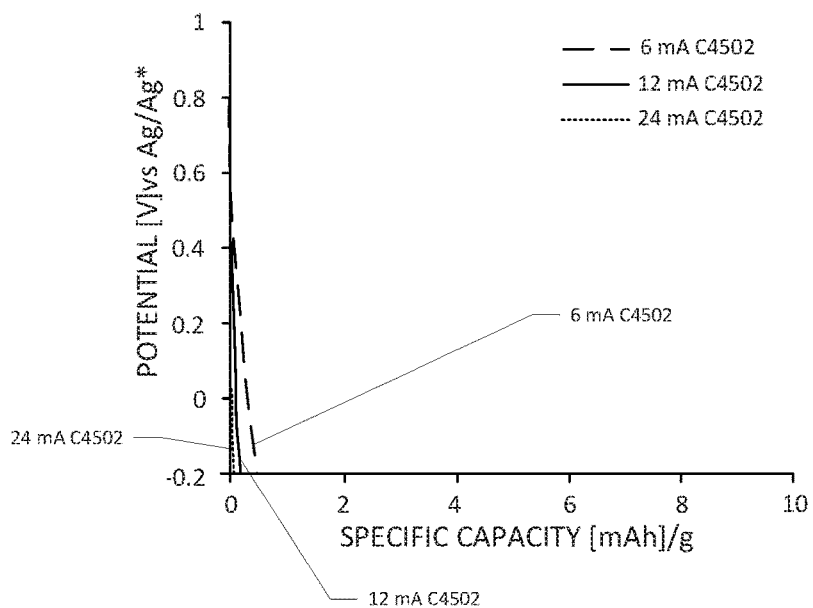
FIG. 5B shows discharge profiles of samples C4502.

FIGS. 5A and 5B show the discharge profiles of the four samples described on FIGS. 4A, 4B, 4C, and 4D, similar to the cyclic voltammetry profiles, C4501 and BQ001 hydrophobic present a higher specific capacity (amount of charge that can be stored) comparing with the rest of the samples.

The second set of experiments aimed to polymerize conducting polymer (Polypyrrole) on the carbon foam in other to increase the capacitance, creating a composite material that can store higher amount of charge. Two different deposition charges, one is 2.68C and the other 13.4C (5 times), were selected. Charge is related to the amount of polymer getting polymerized (mass deposited), although this relationship is not strictly linear as expected in an ideal case.

In aqueous media BQ001 presented a higher capacitance comparing with the rest of the samples (FIG. 2), although in order get the setup of the conditions right, C4501 was used because there is more of this sample than the BQ001.

Figures 6A, 6B, 6C:
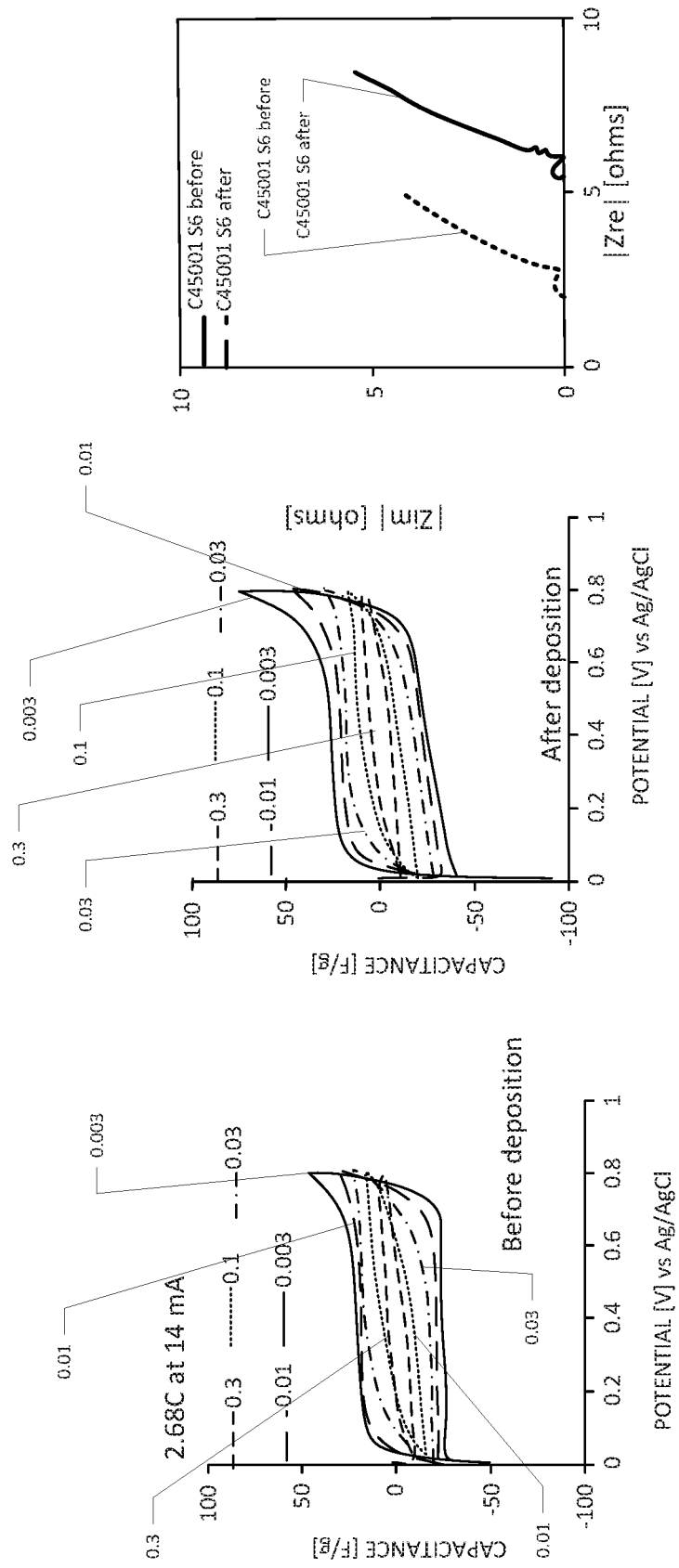
FIGS. 6A and 6B show cyclic voltammetry profiles of carbon foam before (FIG. 6A) and after (FIG. 6B) polymer deposition for 2.68C at 14 mA
FIG. 6C shows a Nyquist plot of real and imaginary impedance comparing before and after deposition.

FIGS. 6A and 6B shows the cyclic voltammetry profiles of C4501 sample before (FIG. 6A) and after (FIG. 6B) the polymer deposition for 2.68C, the latter shows an improvement in capacitance, as well as a significant reduction in the impedance (Nyquist plot, shown in FIG. 6C). Polymer mass deposited: 2.29 mg, total mass of the substrate before deposition: 22.64 mg.

Figures 7A, 7B, 7C:
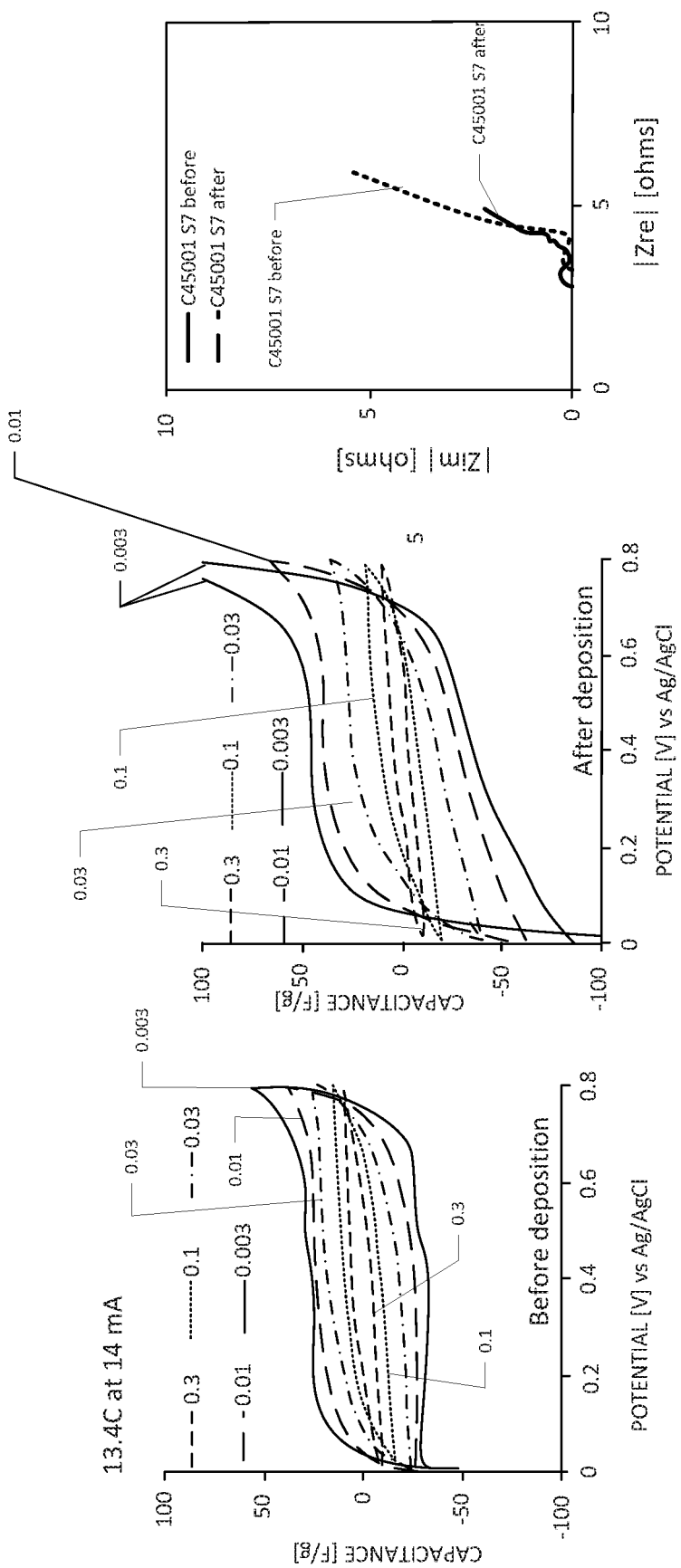
FIGS. 7A and 7B show cyclic voltammetry profiles of carbon foam before (FIG. 7A) and after (FIG. 7B) polymer deposition for 13.4C at 14 mA (reducing current up to 6 mA)
FIG. 7C shows a Nyquist plot of real and imaginary impedance comparing before and after deposition.

FIGS. 7A and 7B show the cyclic voltammetry profiles of C4501 sample before (FIG. 7A) and after (FIG. 7B) the polymer deposition for 13.4C. For this experiment the deposition profile was slightly different, the current was ramped down from 14 to 10 and finally to 6 mA to accomplish the deposition within the ideal deposition potential for pyrrole and trying to avoid any overoxidation of the polymer that can cause a decrease in the performance of the composite material. The CV profile after the deposition presents a significant improvement in the capacitance when compared with the capacitance of the carbon foam by itself. There is also a reduction in the resistance (Nyquist plot, shown in FIG. 7C). Polymer mass deposited: 3.21 mg, total mass of the substrate before deposition: 23.62 mg.

Carbon foams have been tested on different electrolytes (standards for carbon materials) and concentrations to identify in which one shows better electrochemical characteristics, it seems 0.5M $H_2SO_4$ is the best one to study the samples.

Polymerizing the conducting polymer (Pyrrole) on the carbon foam is then tested. SEM micrographs show the polymerization is definitely possible. Identifying the ideal amount to avoid clogging the pores of the foam can be helpful because this can likely cause a decrease in the performance of the carbon foam after depositing polypyrrole.

These same experiments can be performed with a carbon foam sheet and can avoid some of the ion diffusion limitations seen in some of the cyclic voltammetry plots.

Figures 8A, 8B, 8C:
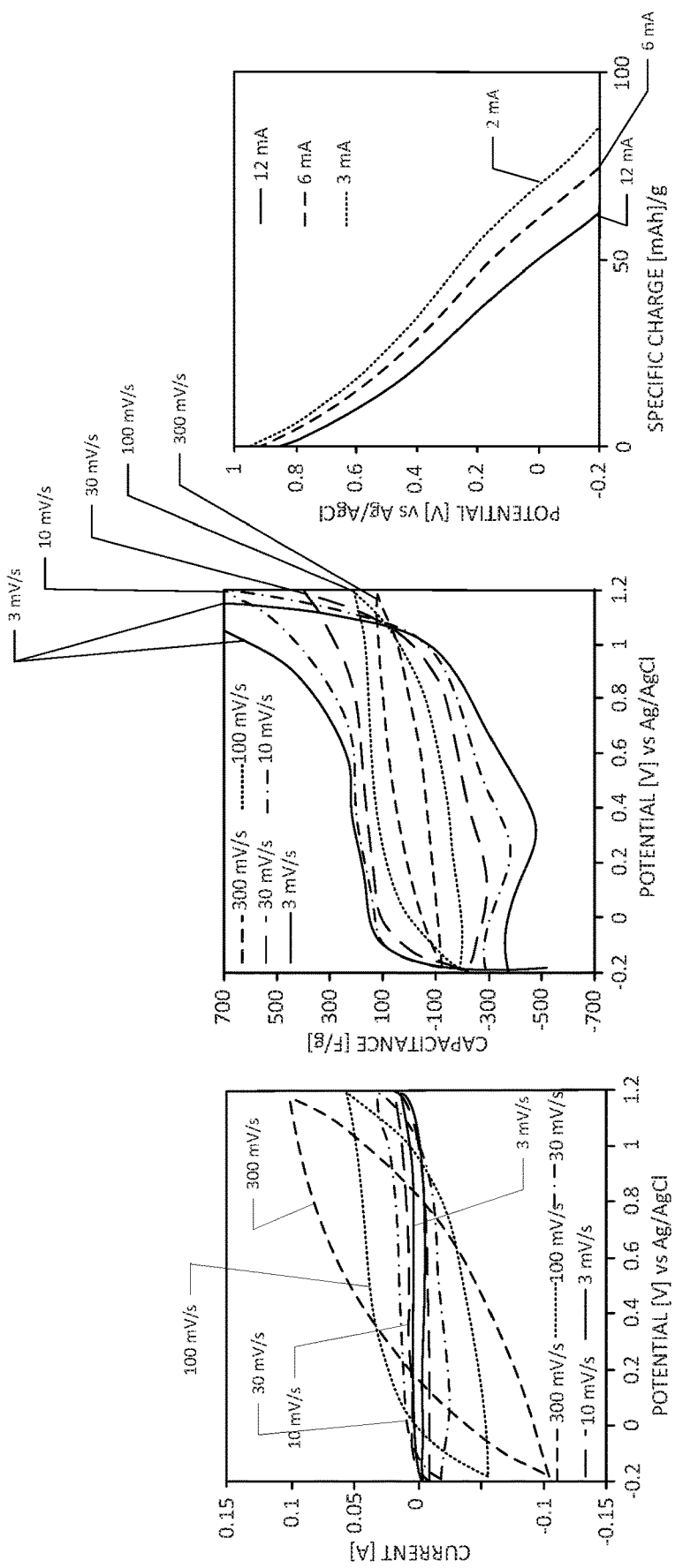
FIGS. 8A and 8B show a carbon foam characterized with Cyclic Voltammetry in 0.5M H2SO4 aqueous solution.
FIG. 8C shows discharge profiles of the carbon foam—sample mass 2.79 mg.

FIGS. 8A and 8B show the comparison with other carbon materials. The fact that the carbon foam shows a Capacitance (amount of charge stored) of about 100-125 F/g for the low scan rates is significant, because not all the carbon materials (mesoporous, activated carbon) depending on the conditions can reach such a high capacitance.

Figure 9A:
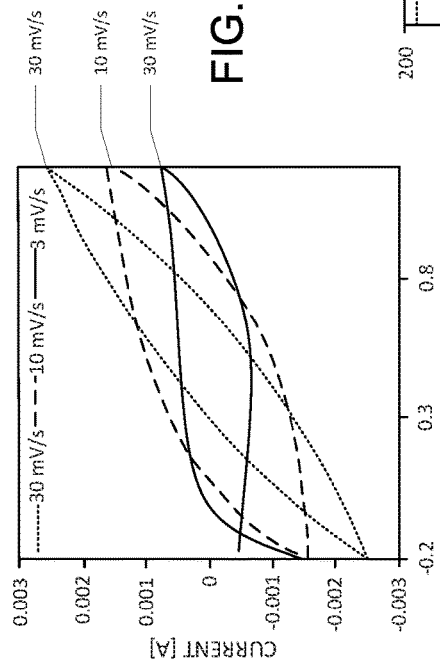
FIGS. 9A and 9B show a carbon foam characterized with Cyclic Voltammetry in 1M $LiClO_4$ in Propylene Carbonate.
Figure 9B:
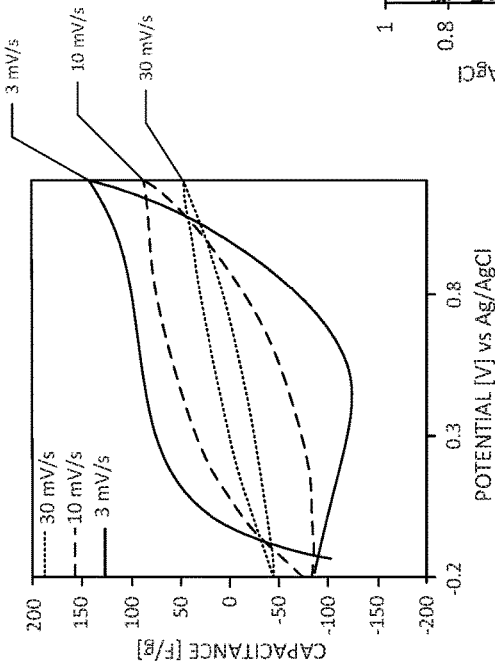
Figure 9C:
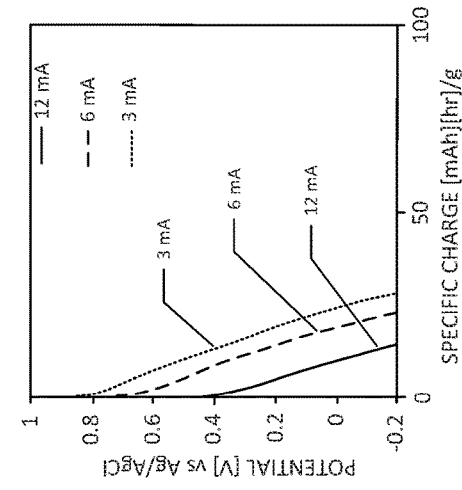
FIG. 9C shows discharge profiles of the carbon foam—sample mass 1.82 mg.

FIGS. 9A and 9B show that organic solvents have a lower conductivity comparing with aqueous solvents, which is part of their limitations, so it is expected that under these conditions the electrochemical performance of the carbon foam can be lower than in aqueous solutions. However, organic solvents allow for a wider voltage range since they are not limited by the decomposition voltage of water (1.23 to −0.83 V).

Figure 10B:
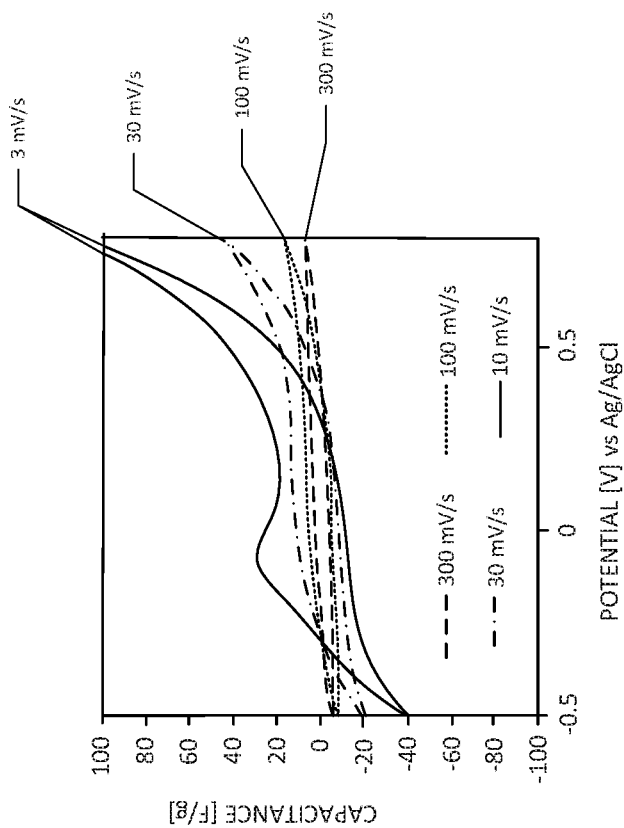
FIGS. 10A and 10B show a carbon foam characterized with Cyclic Voltammetry in 6M KOH aqueous solution—total mass 1.00 mg.
Figure 10A:
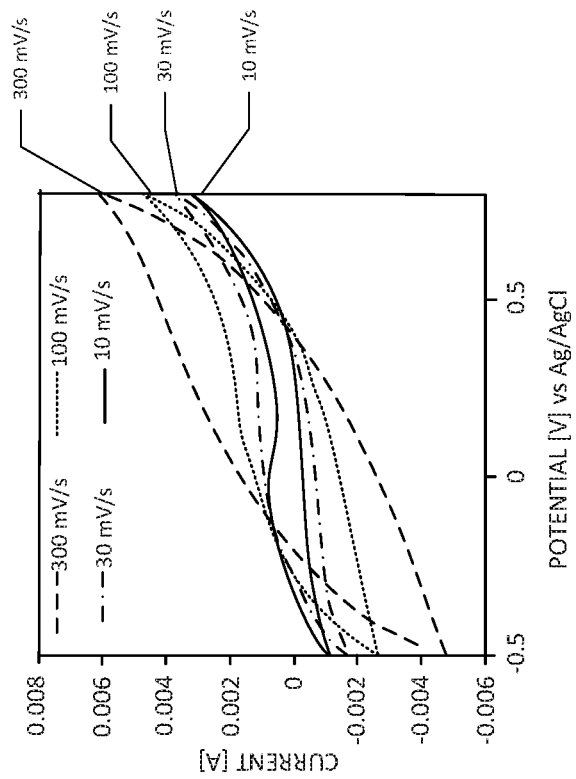
Figure 11A:
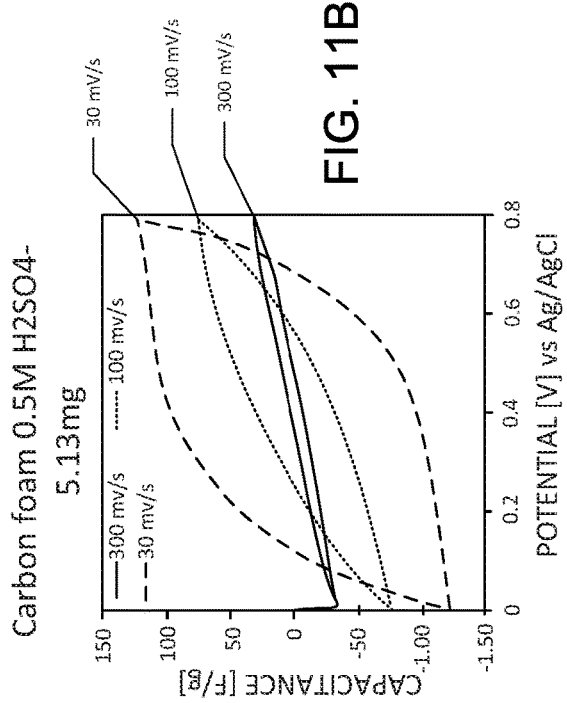
FIGS. 11A, 11B, 11C, and 11D show a carbon Foam+PPy: Cyclic Voltammetry polymerization of pyrrole on carbon foam. Plain carbon foam mass: 5.13 mg (FIGS. 11A and 11B) after polymerization of polypyrrole on its surface 8.94 mg (FIGS. 11C and 11D), 11A and 11B are before polymerization; 11C and 11D are after polymerization.
Figure 11B:
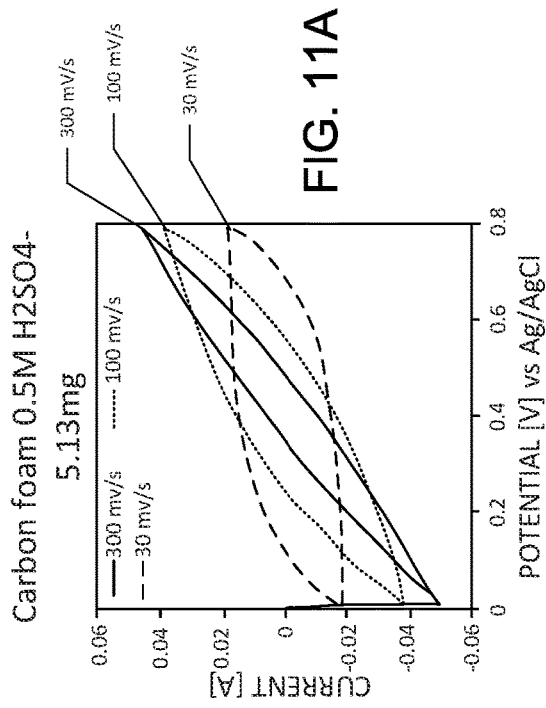
Figure 11C:
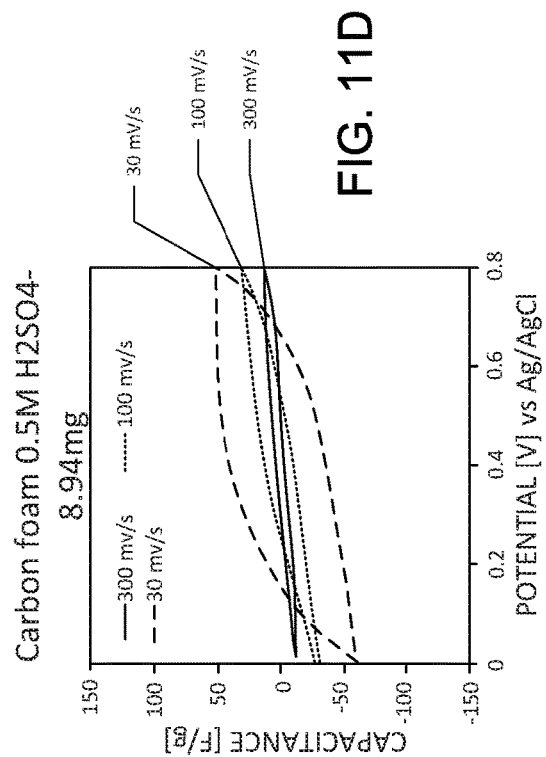
Figure 11D:
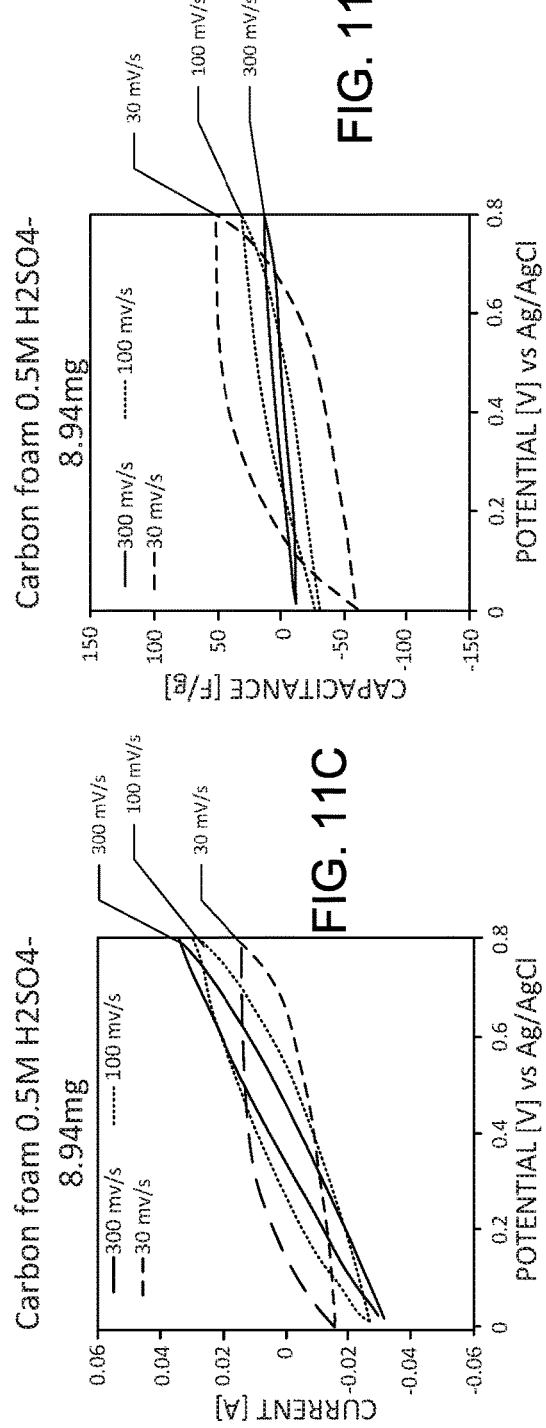

FIGS. 10A and 10B show that KOH is not necessarily a good option for this material.

FIGS. 11A-11D show the cyclic voltammetry polymerization of pyrrole on carbon foam. SEM micrographs show the typical cauliflower structure on the surface, characteristic from polypyrrole deposited by electrochemical polymerization.

Porous resorcinol-formaldehyde foams have been studied since 1989. However, these materials can exhibit significant and sometimes catastrophic shrinkage when dried at ambient conditions without an additional organic solvent exchange step. In some instances, the disclosed process requires no organic solvent exchange step and shrinks approximately 3-4 percent when dried in air at approximately 90° C. Drying at lower temperatures would more than likely produce a similar product with a longer drying time. Additionally, the material created with this process is lyophilic as well as extremely hydrophilic. Some samples have been made that can absorb more than 16 times their weight in water with most samples absorbing approximately 9 times their weight and can experience multiple wetting-drying cycles without significant degradation. These qualities allow for processing of dried resorcinol-formaldehyde foam which heretofore was not possible with the current state of the art. Additionally, after appropriate conditioning, the material became extremely hydrophobic. An example of appropriate conditioning is drying under heat in excess of 100° C. in the presence of a desiccant.

This process accomplishes this through the use of novel catalyst, aluminum salts, which, as yet, have not been evaluated outside of this art. By varying the concentration of catalyst, various pore sizes can be achieved. This process is tunable across a range of pH values, catalyst concentrations and constituent ratios. Varying one or more of these can produce foams with different pore sizes distributions, absorption characteristics, density and possibly carbon yield after pyrolysis.

The open celled foams known in the art had a solidification time of at least 12 hours. The art described here has a solidification time of as little as two hours. If further curing is necessary, it can to a limited extent, be accomplished during the drying step. These two characteristics could lead to a continuous process that incorporates the mixing, curing and drying of the material as opposed to the current state of the art batch process.

The material itself is a light orange to dark red, porous phenolic material with very low bulk density. The void space inside the material is interconnected and made up of pores that range from sizes too small to see under a 50× microscope to several millimeters.

B. Monitoring Device

The U.S. Department of Defense requires infectious disease in vitro diagnostic (IVD) capabilities that are operationally suitable for use in far forward military environments and operationally effective versus a wide range of threats. Current single use disposable Lateral Flow Immunoassay-based diagnostic tests have many desirable operational suitability characteristics (low cost, minimal training, light-weight, results in 15 minutes, eye readable results, and long shelf life at room temperature) but lack sufficient sensitivity to be clinically useful for most infectious diseases. Current nucleic acid amplification-based diagnostic tests provide adequate sensitivity for some diseases but are slow (>30 minutes), more complex, are not compatible with many host response biomarker-based diagnostic approaches and have a high cost per test. The High Sensitivity, Low Complexity, Multiplexed Diagnostic Devices topic seeks to develop novel approaches that will fundamentally improve sensitivity while maintaining desirable operational suitability characteristics. Furthermore, novel approaches will be needed to incorporate multiple analytical approaches into a single platform technology to provide clinical utility across a broad range of etiological agents (i.e., intracellular organisms, parasites, etc.), diseases and clinical sample types and to provide information to support force health protection decision making.

1. Dengue Virus

The disclosed technology can be used to detect any number of things, including viral infections. An example is detection of the Dengue virus. The Dengue virus has four variants DENV1-4, which have a positive single strand RNA genome that directly translates 10 proteins. It is a member of the genus Flavivirus, a genus which also includes such viruses as West Nile virus, yellow fever virus, and Japanese encephalitis, among others. Dengue virus used to be restricted to tropical and subtropical regions, however the exposure region is expanding, affecting 2.5 million people in 110 countries. Of the people infected with Dengue, on average 500,000 will have the potential to develop dengue hemorrhagic fever or dengue shock syndrome.

Dengue is transmitted via mosquito, as such, the virus is endemic to tropical climates. The limiting factor for detecting live virus is the need for the infection to reach a critical viral load in the host. One of the current, and most accurate, strategies for detecting infection is RT-PCR of the viral RNA. While highly sensitive, the method does not lend itself to field work, particularly in tropical regions. An attempt to improve this technology is a variation of RT-PCR, recombinase polymerase amplification (RPA), utilizes a fluorescence probe and isothermic temperatures to detect DENV RNA in as little as 3 minutes. This allows for portability, but still relies on viral titer to meet a threshold. Therefore, while the readout is rapid and the device is portable, the time from infection to detection is still an average of 5 days. One method to shorten detection time is to detect changes in circulating miRNAs as a result of infection.

A previous study found that circulating cytokine levels in infected patients could be detected as early as 6 hours post infection. The cytokine production is heavily regulated at the mRNA level by microRNAs (miRNAS), 22-25 nucleotides in length. The changes in miRNA levels as a result of infection occur upstream to changes in cytokine production, thereby shortening the detection time. The study identified a biomarker of 15 differentially expressed miRNAs, 11 down-regulated and 4 upregulated, in response to DENV2 (and most likely the other DENV variants) infection.

Detection of miRNA in blood, saliva or urine would require either a centralized laboratory, or a novel portable dipstick assay with sensitivity to nucleic acids exceeding the current capabilities of nitrocellulose lateral flow assays.

2. Lateral Flow

Lateral flow immunochromatographic assays have been used to detect a wide variety of antigens in biofluids for decades. Commonly implemented as a dipstick or finger-prick assay, the most familiar application of the technology may be the common pregnancy tests which detect HCG hormones in the 1 ng/mL range.

Figures 12A, 12B, 12C:
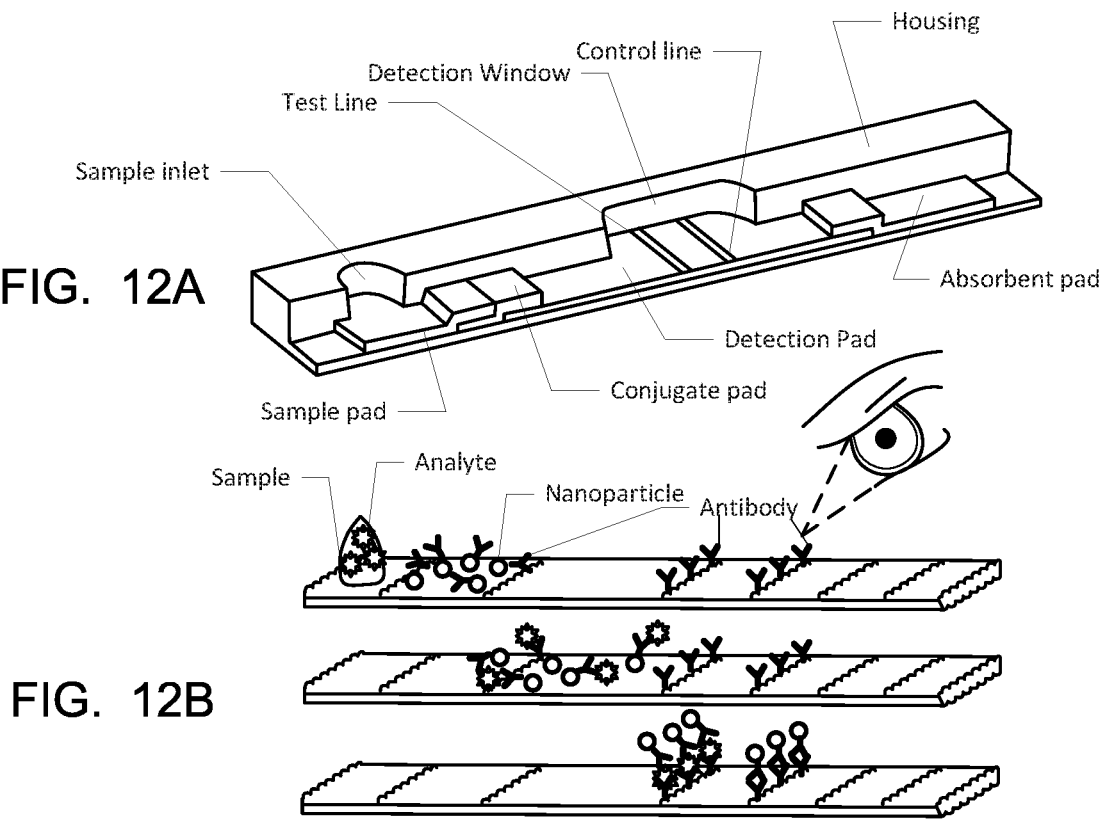
FIGS. 12A, 12B, and 12C show three standard representations of lateral flow immunoassays. The most common lateral flow devices can be read by eye (FIG. 12B), while commercial readers have recently appeared to impart quantitation (FIG. 12C). Their sensitivities are typically not significantly superior to those read by eye, though they do provide some measure of quantitation, if the assay is designed to function as such.

The architecture of a traditional lateral flow dipstick is depicted in FIGS. 12A, 12B, and 12C. The sample is introduced to the sample pad. The treated sample migrates from this region past the conjugate pad, where a contrast-introducing particulate conjugate (either magnetic, colorimetric, or color-shifting) is mobilized from dry form to co-migrate with the sample elution. The conjugate particle is decorated with antigen or antibody, depending on the format of the test and the analyte. As the sample and conjugate particle co-migrate down the nitrocellulose membrane, they pass a control line and a test line. The test line is encountered first, and is decorated on the surface of the nitrocellulose membrane with antigen or antibody to bind the analyte particle, often in the form of a sandwich assay. The bound presence of conjugate particles here represents a positive assay for presence of the analyte. The control line is decorated to nonspecifically bind conjugate particles without requiring the presence of the analyte; conjugate particles here confirm that the system is functioning at the basic levels of performance.

Traditional lateral flow assays rely upon colored latex microparticles or plasmonically colored gold nanoparticles to provide a non-quantitative result. While historically these assays were read by ambient light, as in the case of a home pregnancy test, there have been recent developments of quantitative assays with laser illumination electronic readout devices. In most cases, these techniques are limited to traditional colorimetric assays of gold, silver or latex nanoparticles. Beyond quantitation over a limited range, automated reader technology provides little benefit in terms of sensitivity over reading a lateral flow assay by eye, as scatter/background signal becomes the dominant limiting factor when illumination power is increased. The introduction of upconverting phosphors to lateral flow has provided a relatively background-free detection scheme in recent years, but due to the low diffusion constant of the phosphor-laden upconverting micro-particles, the technique generally requires wet sample prep to achieve high sensitivities. The great benefit of lateral flow is the lack of sample prep or fluidics, which allows for field use. As a result, up-converting lateral flow assays are fundamentally limited, and, as-of-now, an unrealistic option for a field-portable device.

Figure 13A:
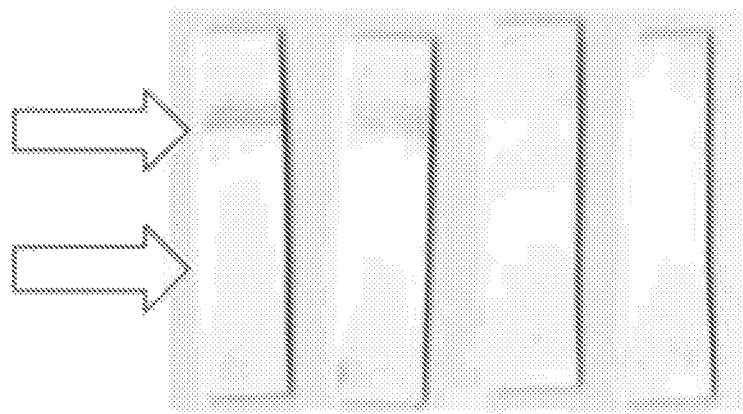
FIGS. 13A and 13B show a representation of lateral flow eye-readability.
Figure 13B:
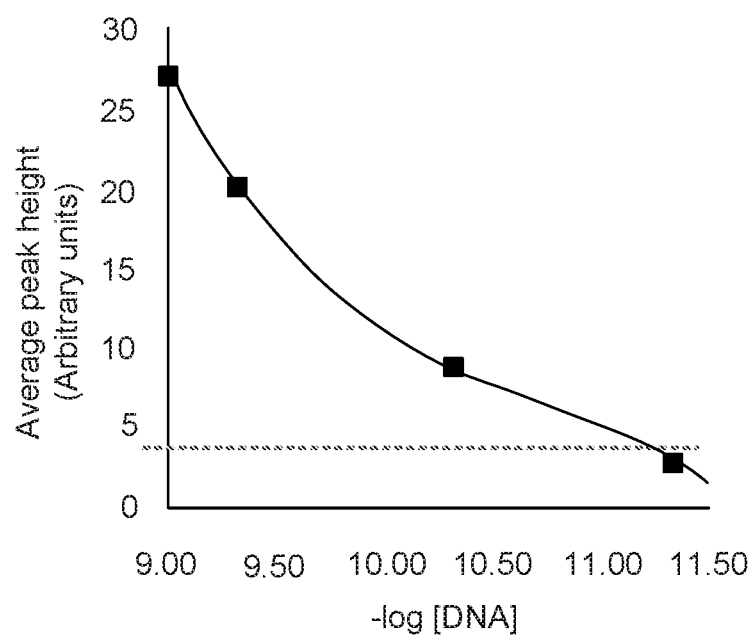
Figure 14:
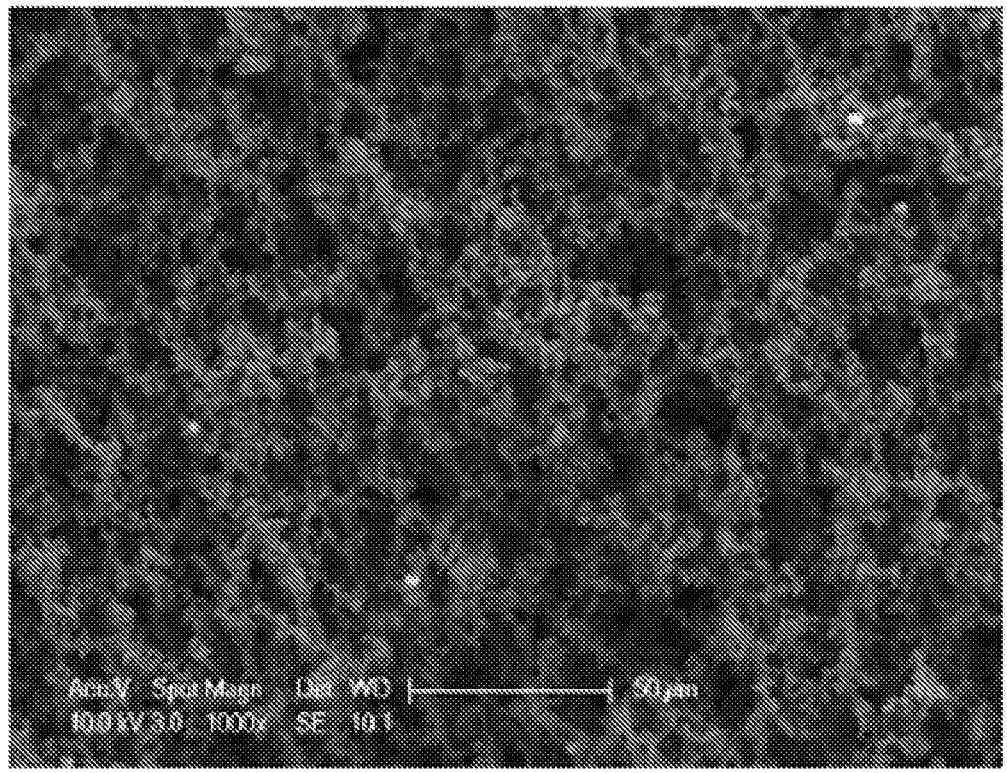
FIG. 14 is a SEM micrograph of one formulation of RF aerogel after carbonization, as produced by SRI. The pore size and optical density of the material can be adjusted over a wide range with simple processing techniques.

Detection of nucleic acids associated with Dengue infection was recently performed in a small, portable lateral flow format without amplification. This work utilized traditional nitrocellulose substrate technology and represented the first published use of unamplified Dengue nucleic acids in a lateral flow format. While this is an important step in detecting Dengue sans amplification, the sensitivity of the experiment was hampered by high background caused by the use of nitrocellulose as the substrate, as concluded by the study's authors (FIGS. 13A and 13B).

Lateral flow test strips can also utilize is Förster (alternatively fluorescence) resonance energy transfer, or FRET. FRET relies upon a donor fluorophore, in this case permanently bound to the control and test regions of the strip, which is excited upon illumination. Upon binding of an acceptor fluorophore tagged analyte, the excited donor may non-radiatively transfer its excitation energy to the acceptor chromophore, and the system emits at the wavelength associated with this acceptor, rather than that of the originally excited donor. FRET or related phenomena are routine methods for the detection of ions, small molecules, proteins or nucleic acids. The model used to describe FRET is Förster theory, the underlying principle of which is based on transition dipole-dipole interactions between the excited donor and acceptor. This interaction has a distance dependence of $1/R^6$, where R is the distance between the donor and acceptor. The efficiency of transfer is therefore highly dependent on distance, and FRET pairs can therefore be utilized as extremely sensitive assays for binding.

Traditionally, FRET has suffered two major drawbacks. First, it is a technique whose fundamental mechanism is extremely sensitive, but whose final sensitivity is limited by sources of noise and background, as it is essentially a ratiometric calculation on low level light signals. Second, FRET traditionally requires advanced optical setups utilizing photomultiplier tubes or cooled CCD cameras.

3. Increased Sensitivity with Novel Aerogel Substrates

A phenolic aerogel was developed via an air dried processing technique which can be made up of either purely phenolic, purely carbon or any state in between while remaining wettable enough to act as a lateral flow substrate. Additionally, the aerogel-based foam has demonstrated tunability to a variety of densities and pore sizes which can be used to create materials that are very efficient wicking agents for a wide variety of fluids. The foams can remove suspended particles while wicking due to the filtering action of the pore structure.

Given the tunability of the pore structure and surface conditions, aerogel makes an attractive alternative to many of the systems currently used in lateral flow assays, including nitrocellulose. Nitrocellulose is a negatively charged porous media that is used in a wide variety of lateral flow assays. However, nitrocellulose presents a number of disadvantages. It has a high scattering coefficient which can cause background signal in any assay, and is a particular problem for FRET. Because the absorption coefficients of aerogels can be tuned from a significant absorber to a nearly perfect absorber when carbonized, aerogels can be made to exhibit extremely low background scattering and auto fluorescence levels.

Furthermore, the aerogel yields a material better suited to lateral flow decoration and nucleic acid immunoassaying than nitrocellulose. While binding to nitrocellulose is poorly understood, it appears to bind hydrophobically. This is not ideal when working with oligonucleotides since these tend to associate poorly with hydrophobic surfaces and the hydrophobic binding can affect the shape of the bound molecule which could cause it to either behave unpredictably or denature entirely. In contrast, the aerogel system proposed here is a polymer that can range in color from light orange to black and presents a high density of hydroxyl groups, which can be used as covalent binding sites.

4. Prepare a Range of Aerogel Formulations Suitable for Lateral Flow FRET Use

Aerogels are open cellular foams known for extremely high porosity and surface area. Originally developed in the 1980's, phenolic aerogels are formed from a metal ion catalyzed condensation reaction of resorcinol with formaldehyde into a cross-linked network of spheres which can be heated to over 1000° C. in an inert environment to create a carbon foam of identical dimensions.

These materials have shown great promise but have suffered from a number of processing and durability limitations, for example the structure shrinks catastrophically when dried due to capillary forces. To preserve the structure, expensive and difficult processes are required such as nonpolar solvent exchange, freeze drying or super critical $CO_2$ washing. Recently, a new catalyst formula has been developed for a phenolic foam processing that can be air dried and subsequently processed using either wet chemistry or heat treatment under various conditions. The pore size, pore size distribution and wicking characteristics have been shown to be reproducibly alterable by varying the ratios of constituent parts without affecting the underlying chemical structure.

The current study involves a) optimizing chemistry of the material to provide an optimized pore size to facilitate wicking while exhibiting the highest possible visible surface area and b) optimizing the heat treatment to reduce the noise signal while maintaining an acceptable number of binding sites.

i. Optimizing Chemistry of the Material to Provide an Optimized Pore Size

The pore size can be altered by varying the ratio of resorcinol to catalyst while maintaining the ratio of resorcinol to formaldehyde and resorcinol to water. The optimal pore size is one that effectively wicks the analyte solution through the pore space without filtering the analyte while providing a large, non-shadowed, surface area. The wicking can be evaluated by introduction of analyte solution into the material with various pore sizes. In each case, the amount of fluid absorbed and the wicked height can be measured. The available surface area for each pore size can be directly labeled with a fluorophore and excited using a laser. Increased fluorescent response can be indicative of an increased surface area, assuming the number of functional groups is held constant.

This can be expanded upon by the introduction of actual blood to judge the material's ability to remove extraneous matter such as red blood cells. A layered pattern of size-exclusion layers is envisioned to effectively remove large solids and improve the clarity of the test.

ii. Optimizing the Heat Treatment

The number of binding sites (hydroxyl groups) present on the material can first be established in a fully cured sample prior to heat treatment and in a fully carbonized sample that has no binding sites present. Auto fluorescence can also be measured for these samples. Samples can be produced and heat treated to higher temperatures in 100° C. increments. These samples can both be tested for hydroxyl group density and autofluorescence as well.

5. Functionalize and Optimize Aerogel for FRET (SRI, RMD)

The oligonucleotide probes to be covalently linked to the functionalized aerogel can be modified to have donor and acceptor fluorescent probes at the 5' and 3' ends respectively. These probes can allow for the utilization of FRET, whereby the donor fluorophores transfer their excited state to the excitation energy level of an acceptor fluorophore. The resultant emission intensity change upon binding is captured and digitized into a quantifiable signal. Because of this energy transfer, the system can be multiplexed to use one excitation wavelength to transfer energy to a handful of potential acceptor fluorophores. Cyan Fluorescent protein, or CFP, is the most versatile donor as it can excite both green and red fluorescent protein (GFP and RFP) acceptors. However, the size of these proteins is not conducive to binding free miRNA.

Listed below in table 1 is a list of common donor/acceptor pairs, with fluorescein being the most versatile donor.

TABLE 1

Common donor/acceptor pairs

| Donor | Acceptor | $R_o$ (Å) |
| --- | --- | --- |
| Fluorescein | Tetramethylrhodamine | 55 |
| IAEDANS | Fluorescein | 46 |
| EDANS | Dabcyl | 33 |
| Fluorescein | Fluorescein | 44 |
| BODIPY FL | BODIPY FL | 57 |
| Fluorescein | QSY 7 and QSY 9 dyes | 61 |

Figure 15:
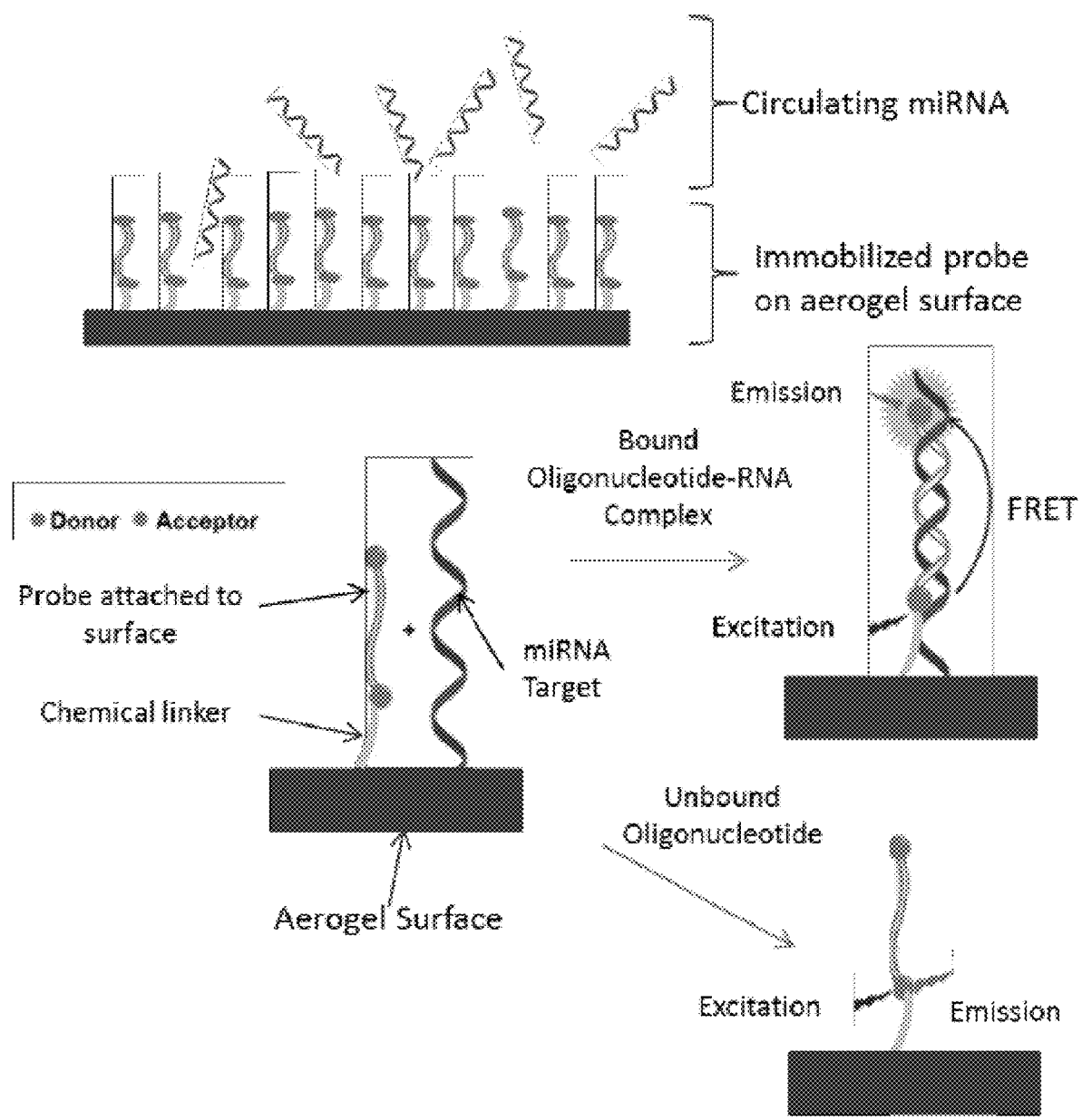
FIG. 15 shows miRNA detection by FRET on an aerogel substrate.

The proper alignment of the donor and acceptor fluorophores occurs when the complimentary RNA strand binds the probe, locking the orientation. Use of a common donor simplifies the design by necessitating only one excitation wavelength. A diagram of the proposed probe-RNA binding and subsequent FRET can be seen in FIG. 15.

Initial characterization of an aerogel substance by optical study: Samples of the aerogel can be examined for their suitability for chemical functionalization by Fourier Transform Infrared Spectroscopy [FTIR]. The surface density of hydroxyl groups on the convoluted folds of the aerogel can be analyzed as a primary determinant of assay efficiency.

The appropriate sample preparation technique for the aerogel samples is to grind them to a fine powder and examine each sample by the Attenuated Total Reflection [ATR] sample handling technique. The intensity of the hydroxyl group absorption (3550-3200 $cm^{-1}$; a broad, strong signal) in the FTIR as a function of carbonization temperature in 100° C. increments to develop an understanding of the density of phenol hydroxyl groups available for chemical reaction and chemical derivation to attach signaling oligonucleotides. In FIG. 4A, how to ascertain the reactivity of the phenolic hydroxyl groups by treating the aerogel sample with acetyl chloride in an appropriate chlorocarbon solvent (such as methylene chloride or chloroform) is shown. With FTIR, the amount of hydroxyl group absorption remaining after chemical reaction with acetyl chloride and the appearance of the ester carbonyl absorption can be measured. The intensity of the ester carbonyl absorption (1750-1735 $cm^{-1}$; a sharp, strong signal) will be the reciprocal of the decrease in intensity of the phenol hydroxyl group absorption.

The samples can be further characterized for scattering and autofluorescence at FRET excitation wavelengths, as well as structural integrity and retention of wicking characteristics. Several formulations optimized to provide the best compromise between available reactive hydroxyl functionality, low autofluorescence, reduced scattering background, and structural integrity can be chosen for use in the chemical derivatization studies.

Derivatization of the aerogel: A number of chemical techniques can be used to derivatize the aerogel substrate for the attachment of a signaling moiety such as miRNA. One method is used in the context of oligonucleotide conjugation to inorganic and biological substrates and is known as 'copper free click chemistry'. This involves the reaction of an organic azide attached to the aerogel substrate by an ester, carbonate or carbamate group with a strained and reactive triple bond attached to a signaling oligonucleotide. Click chemistry is a clean and high yielding method for modular derivatization. The success of these reactions can be followed by FTIR to examine the absorptions associated with ester formation (1750-1735 $cm^{-1}$), the azide group (2210-2200 $cm^{-1}$) and the triazole product of the reaction (1580-1550 $cm^{-1}$, 1490-1410 $cm^{-1}$) between the azide and triple bond.

Figure 16A:
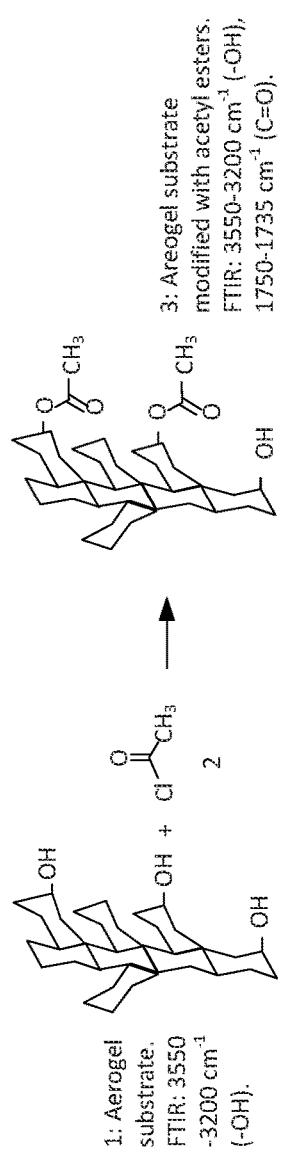
FIGS. 16A and 16B show a proposed Click chemistry of labeling aerogel for FRET use.

This process is illustrated in FIG. 16A. The unmodified aerogel substrate (1) is reacted with the organic azide (4) by formation of an ester bond through the reaction of the acid chloride group in 4 with the available phenolic hydroxyl groups on 1 to give 5, the aerogel modified with the organic azide. Likely solvents for this reaction include dichloromethane ($CH_2C_{12}$) or chloroform ($CHCl_3$).

Figure 16B:
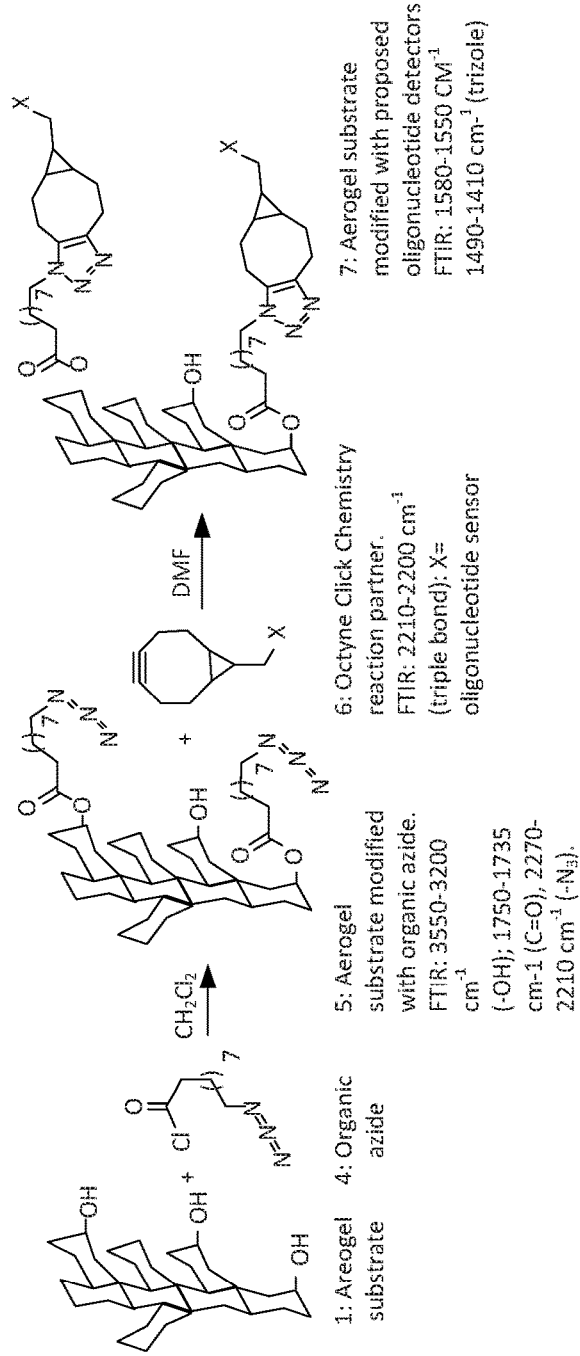
Figure 17:
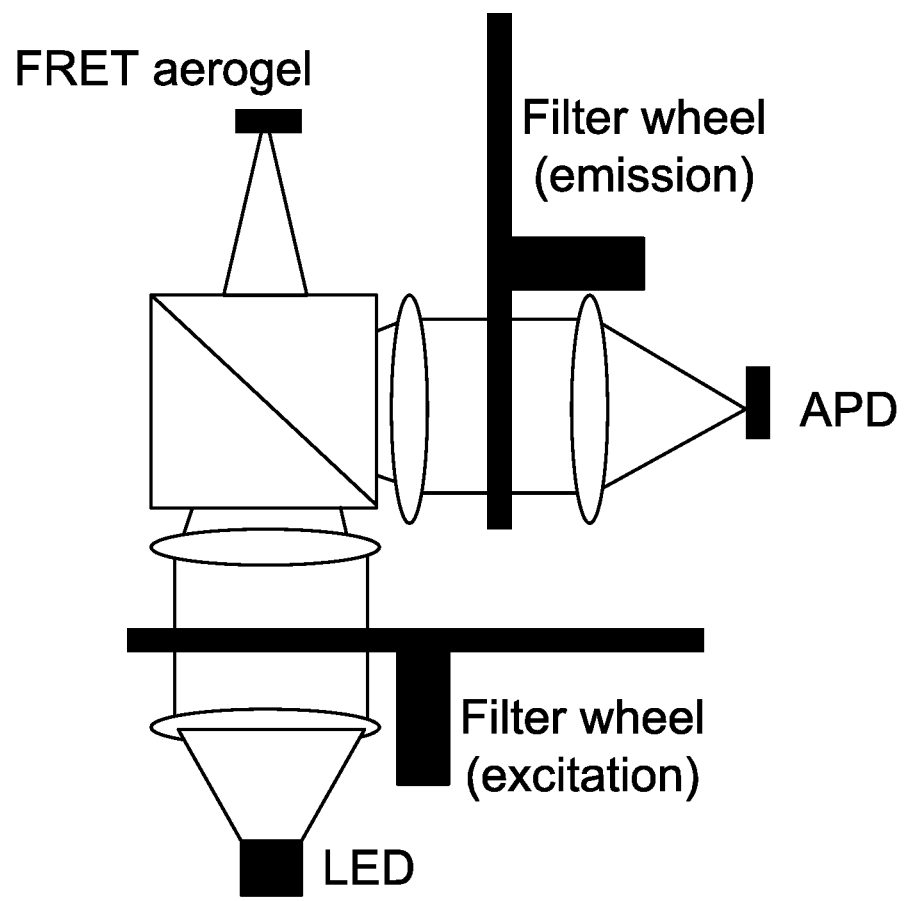
FIG. 17 is a diagram of initial optical evaluation setup in phase I. Collimation can be adjusted evaluate efficacy of filters at varying numerical apertures, as a compact system will trade collimation for complexity.

In FIG. 16B, the reaction of 5 with the octyne click chemistry partner 6 will give aerogel substrate modified with the oligonucleotide detector 7. This reaction should take place at ambient temperature or with mild heating (not more than 100° C.); a solvent that can accommodate both the aerogel 5 and octyne modified oligonucleotide 6 would be the polar aprotic solvent such as dimethylformaide (DMF) or acetonitrile.

The required octyne-derivatized oligonucleotide detector 6 can be prepared from a commercially available octyne by a method disclosed in US 2013/0066063 A1. This method is very convenient because it discloses exactly the use of the starting material and describes how this compound can be derivatized with short miRNA sequences prepared by standard solid phase nucleoside synthesis techniques. The short miRNA sequences can be readily derivatized to incorporate the appropriate fluorophore acceptor/emitter pair using standard methods.

Fluorescence evaluation: Samples functionalized with acceptor fluorophores can be evaluated for relative density of fluorophore loading and detection efficiency. Aerogel samples can be mounted and illuminated with collimated light from a LED chosen for overlap with the excitation envelope of the donor fluorophore. A spectrometer can be utilized (Acton 2100i) to couple isotropic light at a close distance with matched objective lenses or alternatively a round-to-slit fiber bundle. Samples can be evaluated for total fluorescent yield and uniformity, and can be tuned to maximize yield by maximizing surface area and reaction site density, while minimizing the effect of shadowing due to convolution and increased optical density upon carbonization.

6. Prepare Infectious Analytes or Substitute Model Systems with Acceptor Fluorophore Tagging Chemistry Completed The analyte preparation can be based on the Dengue biomarker miRNAs known in the art. The 5 miRNA probes can be commercially synthesized to contain the same 5' donor, but unique 3'acceptors so that each can be detected individually. A master mix of the miRNA probes can be made in excess to saturate the available functional binding sites on the aerogel. To test the ability of miRNAs to bind the probes and allow for fluorescence, oligonucleotides can be synthesized based on the mature miRNA sequences (obtained from miRbase.org). These synthesized oligos can also be used to test the lateral flow, and wicking capacity of the probe-coated aerogel so as to optimize the pore structure as described above.

Specifically, the 5 most significantly altered miRNAs can be used as an indicator of exposure to the Dengue Virus. Examples of proposed miRNA targets are: heavily upregulated-miR-4290, -let-7e, -1290 and -33a; and heavily downregulated-miR-106b The corresponding mRNA sequence target for each miRNA, fluorescently labeled, can be attached to the aerogel. The binding of the miRNA to its target sequence can confer a conformational change to the fluorescent probe, and using FRET can allow for detecting binding via emission of the acceptor fluorophore. The extent of the signal can be digitized and reported as a measure of the abundance of miRNA in the sample. The device can provide a truly portable, no processing method of detecting DENV infection as close to the onset as possible by detecting changes in the levels of circulating miRNA.

7. Perform Bench Testing of Optical Detection Scheme and Refine for Miniaturization The field portability and eye readability of a multiplexed assay either requires a complex pattern and/or color scheme to be subjectively analyzed by untrained users, or a small, inexpensive and robust battery-operated electro-optical reader system which quantitatively interprets results and presents the user with reduced data. The final prototype tested in Phase II and beyond will include one of two methods of multiplexing. The first is a led or laser array and a matching avalanche photodiode array, with an array of corresponding filters which are slid along a simple linear encoder, thereby allowing for digital readout of each fluorophore individually in each well. The second method involves a small spectrometer chip developed via holographic grating technology. This chip allows for high efficiency spectral analysis in a compact, low cost silicon-based package. This single chip is suited to the multiplexing of analytes in a single well as limited only by the fluorescent label.

In this task, illumination by laser and LED and readout by avalanche photodiode can be evaluated for technical feasibility and lower limit of sensitivity of the aerogel FRET assay. Illumination can be adjustable between collimated and focused at a distance of 50 mm, and presented to the aerogel at both 45° and 0°. Titrations of prepared miRNA analytes can be presented to the aerogel and remain unrinsed.

Filtration of LED light can be compared with technologies filtering more collimated laser light, and an effective solution to filtering will be determined. If no filter media can be found to effectively allow for a sensitive FRET assay, then spectrometer-on-chip integration can proceed to enable full scale prototyping.

A wide variety of avalanche photodiodes (APDs) are arrayable on chips less than 400 microns in thickness and are biased with less than 40 V while providing gains in excess of $10^6$. These photodiodes can be evaluated for suitability to tiling.

Detecting one infectious agent (in this case miRNA characteristic to Dengue infection can be considered successful if detection can be performed at $10^{-9}$ M, or two orders of magnitude more sensitive than previous Dengue nucleic acid detection studies. Work to increase sensitivity to clinically relevant levels ($10^{-11}$ to $10^{-15}$ M) can include not only optimization of the aerogel labeling and the detection system, but possibly also the pre-concentration of nucleic acids similar to an orthosilicate concentration step.

8. Validate Suitability of Instrument for Multiplexing Multiple Analytes via a Second FRET Pair and/or Physical Separation of Analytes in a Multiwall Plate Assay Probes for a certain analyte can be fixed to the surface and the resultant fluorescent material can be tested as described above. However, miRNA fingerprints require that several fluorescent probes bind several types of miRNA for a successful assay. Given the wide variety of probes and donor/acceptor pairs available, using emission colors is a viable solution with the difficulty being resolving the various colors becomes more difficult as the number of colors increases. In this way, a single assay is analogous to a full, multiplexed detector.

Tests can be run to detect the presence of multiple miRNA strands using multiple probe-acceptor/donor systems fluorescing multiple emission colors. Patterning the various probes, all of which use the same donor acceptor pair spatially across the material can also be an effective solution.

Various modifications and variations can be made to the compounds, composites, kits, articles, devices, compositions, and methods described herein. Other aspects of the compounds, composites, kits, articles, devices, compositions, and methods described herein will be apparent from consideration of the specification and practice of the compounds, composites, kits, articles, devices, compositions, and methods disclosed herein. It is intended that the specification and examples be considered as exemplary.

We claim:

1. A method comprising the steps of:
    a) providing an aerogel comprising a polyhydroxy benzene compound crosslinked with formaldehyde, wherein the aerogel is dry and has a first volume, wherein the aerogel can be exposed to a liquid and be re-dried in a gas while retaining at least 70% of the first volume; and
    b) modifying a hydroxyl group on the polyhydroxy benzene compound crosslinked with formaldehyde with a chemical linker comprising a reactive moiety comprising an alkyne or an azide, thereby producing a functionalized aerogel,
    wherein the chemical linker is further bound to a signaling moiety via the alkyne or the azide via click chemistry, wherein the functionalized aerogel comprises the aerogel, the chemical linker, and the signaling moiety, wherein the chemical linker is bound to both the signaling moiety and the aerogel.

2. The method of claim 1, wherein the aerogel is hydrophilic.

3. The method of claim 1, wherein the aerogel is hydrophobic.

4. The method of claim 1, wherein the reactive moiety is an alkyne.

5. The method of claim 1, wherein the reactive moiety is an azide.

6. The method of claim 1, wherein the signaling moiety comprises a detection portion and a target binding portion.

7. The method of claim 6, wherein the detection portion comprises a fluorescent moiety, acolloidal gold, an enzyme, a dye, a radioisotope, or a chemiluminescent marker.

8. The method of claim 6, wherein the target binding portion comprises a RNA molecule, a DNA molecule, an antibody, or fragment thereof.

9. The method of claim 1, wherein the polyhydroxy benzene compound is resorcinol.

10. The method of claim 1, wherein the molar ratio of the polyhydroxy benzene compound to formaldehyde in the provided aerogel is from about 1:1 to about 1:4.

11. The method of claim 1, wherein the provided aerogel can be exposed to a liquid and be re-dried in air while retaining at least 90% of the first volume.

12. A method comprising the steps of:
    a) providing an aerogel consisting of a polyhydroxy benzene compound crosslinked with formaldehyde, wherein the aerogel is dry and has a first volume, wherein the aerogel can be exposed to a liquid and be re-dried in a gas while retaining at least 70% of the first volume; and
    b) modifying the aerogel with a chemical linker comprising a reactive moiety comprising an amine, an amide, an azide, an alkane, an alkene, an alkyne, or a thiol, wherein the chemical linker does not comprise a silane, thereby producing a functionalized aerogel.

13. The method of claim 12, wherein the aerogel is hydrophilic.

14. The method of claim 12, wherein the aerogel is hydrophobic.

15. The method of claim 12, wherein the signaling moiety comprises a detection portion and a target binding portion.

16. The method of claim 15, wherein the detection portion comprises a fluorescent moiety, acolloidal gold, an enzyme, a dye, a radioisotope, or a chemiluminescent marker.

17. The method of claim 15, wherein the target binding portion comprises a RNA molecule, a DNA molecule, an antibody, or fragment thereof.

18. The method of claim 12, wherein the polyhydroxy benzene compound is resorcinol.

19. The method of claim 12, wherein the molar ratio of the polyhydroxy benzene compound to formaldehyde in the provided aerogel is from about 1:1 to about 1:4.

20. The method of claim 12, wherein the provided aerogel can be exposed to a liquid and be re-dried in air while retaining at least 90% of the first volume.

* * * * *